(12) United States Patent
Chiu et al.

(10) Patent No.: US 9,023,599 B2
(45) Date of Patent: May 5, 2015

(54) **METHOD OF DETECTING THE PRESENCE OF PNEUMOCOCCAL NEURAMINIDASES IN *STREPTOCOCCUS PNEUMONIAE*-INFECTED SAMPLES**

(71) Applicants: Cheng-Hsun Chiu, Taoyuan (TW); Rajendra Prasad Janapatla, Taoyuan (TW); Chyi-Liang Chen, Taoyuan (TW); Mei-Hua Hsu, Taoyuan (TW); Hsiu-Ling Chen, Taoyuan (TW); Chung-Tsui Huang, Taoyuan (TW); Hsin-Ju Chang, Taoyuan (TW); Wan-Ting Liao, Taoyuan (TW)

(72) Inventors: Cheng-Hsun Chiu, Taoyuan (TW); Rajendra Prasad Janapatla, Taoyuan (TW); Chyi-Liang Chen, Taoyuan (TW); Mei-Hua Hsu, Taoyuan (TW); Hsiu-Ling Chen, Taoyuan (TW); Chung-Tsui Huang, Taoyuan (TW); Hsin-Ju Chang, Taoyuan (TW); Wan-Ting Liao, Taoyuan (TW)

(73) Assignee: Chang Gung Medical Foundation, Linkou Branch, Taoyuan (TW)

( * ) Notice: Subject to any disclaimer, the term of this patent is extended or adjusted under 35 U.S.C. 154(b) by 0 days.

(21) Appl. No.: 13/775,263

(22) Filed: Feb. 25, 2013

(65) Prior Publication Data
US 2014/0242591 A1   Aug. 28, 2014

Related U.S. Application Data

(62) Division of application No. 13/244,482, filed on Sep. 25, 2011.

(51) Int. Cl.
*C12Q 1/68* (2006.01)
*A61K 39/09* (2006.01)
*G01N 33/569* (2006.01)
*G01N 33/573* (2006.01)
*C07K 16/12* (2006.01)
*C07K 16/40* (2006.01)
*A61K 39/00* (2006.01)

(52) U.S. Cl.
CPC  *C12Q 1/689* (2013.01); *C12Q 1/68* (2013.01); *A61K 39/092* (2013.01); *A61K 2039/55566* (2013.01); *G01N 33/56944* (2013.01); *G01N 33/573* (2013.01); *C07K 16/1275* (2013.01); *C07K 16/40* (2013.01)

(58) Field of Classification Search
CPC ......................................................... C12Q 1/68
USPC ............................................................ 435/6.1
See application file for complete search history.

(56) References Cited

U.S. PATENT DOCUMENTS

| 4,231,750 | A  | * | 11/1980 | Dowben et al. | ................ 436/546 |
| 5,571,682 | A  | * | 11/1996 | Jacobs et al. | .................... 435/7.9 |
| 7,460,960 | B2 | * | 12/2008 | Lee et al. | ......................... 702/27 |

* cited by examiner

*Primary Examiner* — Ardin Marschel

(57) ABSTRACT

A method of providing protection against pneumococcal infection in a subject is disclosed. The method includes steps of administering to the subject a composition that includes combination of three recombinant pneumococcal neuraminidases: NanA, NanB, and NanC of *S. pneumoniae* strains CGSP14, wherein administration of the recombinant pneumococcal neuraminidases elicits an immune response to *S. pneumoniae*, and treats the subject. In one embodiment, the method further includes a step of adding adjuvants to enhance the immune response. The method also includes a step of using passive antibodies, wherein said passive antibodies are anti-neuraminidase antibodies generated from neuraminidases-immunized humanized animals: NanA, NanB, and NanC. Meanwhile, this invention also provides a method for the molecular diagnosis of pneumococcal infection.

2 Claims, 14 Drawing Sheets

SEQUENCE LISTING

<160> NUMBER OF SEQ ID NOS: 6

<210> SEQ ID NO 1
<211> LENGTH: 2943
<212> TYPE: DNA
<213> ORGANISM: Streptococcus pneumoniae strain CGSP14

<400> SEQUENCE: 1

```
atgtcttatt tcagaaatcg ggatatagat atagagagga tcagtatgaa tcggagtgtt      60
caagaacgta agtgtcgtta tagcattagg aaactatcgg taggagcggt ttctatgatt     120
gtaggagcag tggtatttgg aacgtctcct gttttagctc aagaaggggc aagtgagcaa     180
cctctggcaa atgaaactca actttcgggg gagagctcaa ccctaactga tacagaaaag     240
agccagcctt cttcagagac tgaactttct ggcaataagc aagaacaaga aaggaaagat     300
aagcaagaag aaaaaattcc aagagattac tatgcacgag atttggaaaa tgtcgaaaca     360
gtgatagaaa aagaagatgt tgaaaccaat gcttcaaatg tcagagagt tgatttatca      420 agtgaactag ataaactaaa gaacttgaa aacgcaacag ttcacatgga gtttaagcca      480
gatgccaagg ccccagcatt ctataatctc ttttctgtgt caagtgctac taaaaaagat     540
gagtacttca ctatggcagt ttacaataat actgctactc tagaggggcg tggttcggat     600
gggcaacagt tttacggtaa ttacaacgat gcacccttaa aagttaaacc aggtcagtgg     660
aattctgtga ctttcacagt tgaaaaaccg acagcagaac tacctaaagg ccgagtgcgc     720
ctctacgtaa acggggtatt atctcgaaca agtctgaaat ctggcaattt cattaaagat     780
atgccagatg taacgcatgt gcaaatcgga gcaaccaagc gtgccaacaa tacggtttgg     840
gggtcaaatc tacagattca gaatctcact gtgtataatc gtgctttaac accagaagag     900
gtacaaaaac gtagtcaact ttttaaacgc tcagatttag aaaaaaaact acctgaagga     960
gcggttttaa cagagaaaac ggacatattc gaaagcgggc gtaacggtaa accaaataaa    1020
gatggaatca agagttatcg tattccagca cttctcaaga cagataaagg aactttgatc    1080
gcaggtgcag atgaacgccg tctccattcg agtgactggg gtgatatcgg tatggtcatc    1140
agacgtagtg aagataatgg aaagacatgg ggagataagg tggttatctc caatcttcga    1200
gataatcctg aagctaaaga tcctgctgcg ccatcgcctc taaatattga tatggttttg    1260
gttcaagacc cgacaacaaa gagaatcttc tcaatttatg atatgttccc agaaggtcga    1320
gcagtttttg gaatgccaaa aacacctgaa aaagcttatg aaaagatagg ggataaaact    1380
tatcaaatct tgtataaaca aggagagtct ggtcattata ctgttcgtga aatggagaa     1440 gtgtataatg cacaaaatca aaagacggat tatcgtgttg tagtgaatcc aacagaacct    1500
ggctatagag ataaaggaaa tctttacaaa ggtcaggaat tgattggaaa tatctatttt    1560
gcacacagta caaaaaatcc atttagagta gccaatacga gctatctatg gatgtcatat    1620
agtgacgatg atggtaaaac ttggtctgca ccgagagaca ttactccagg tcttcgcaag    1680
gattggatga gttcctagg aacaggtcct ggaacaggaa ttgtacttcg gaatgggcct    1740
cacaagggac ggattttgat accggtttat acgactaata atgtatctca cttaaatggc    1800
tcgcaatctt ctcgtgtcat ctattcagat gatcatggaa aaacttggca tgctggagaa    1860
gcggtcaacg ataaccgtca ggtagacggt caaaagatcc actcttctac gatgaacaat    1920
gaacgtgcgc aaaatacaga atcaacggtg gtacaactaa acaatggaga tgttaaactc    1980
tttatgcgtg gtttgactgg agatcttcag gttgctacaa gtaaagacgg aggagtgact    2040
tgggagaagg atatcaaacg ttatccacag gttaaagatg tctatgttca aatgtctgct    2100
```

| | |
|---|---|
| atccatacga tgcacgaagg aaaagaatac atcatcctca gtaatgcagg tggaccgaaa | 2160 |
| cgtgaaaatg ggatggtcca cttggcacgt gtcgaagaaa atggtgagtt gacttggctc | 2220 |
| aaacacaatc caattcaaaa aggagagttt gcctataatt cgctccaaga attaggaaat | 2280 |
| ggggagtatg gtatcttgta tgaacatact gaaaaaggac aaaatgccta tacccctatca | 2340 |
| tttagaaaat ttaattggga cttttgagc aaagatctga tttctcctac cgaagcgaaa | 2400 |
| gtgaagcgaa ctagagagat gggcaaagga gagatgggca aaggagttat ggcttggag | 2460 |
| ttcgactcag aagtattggt caacaaggct ccaacccttc aattggcaaa tggtaaaaca | 2520 |
| gcgactttcc taacccagta tgatagcaag accttgttgt ttgcagtaga taggaagat | 2580 |
| atcggacagg aaattattgg tatagctaaa ggaagcatcg aaagtatgca taatcttcct | 2640 |
| gtaaatctag caggtgccag agttcctggc ggagtaaatg gtagcaaagc agcggtgcat | 2700 |
| gaagttccag aatttacagg gggagttaat ggtacagagc cagctgttca tgaaatcgca | 2760 |
| gagtataagg gatctgattc gcttgtaact cttactacaa aagaagatta tacttacaaa | 2820 |
| gctcctcttg ctcagcaggc acttcctgaa acaggaaaca aggagagtga cctcctagct | 2880 |
| tcactaggac taacagcttt cttccttggt ctgtttacgc tagggaaaaa gagagaacaa | 2940 |
| taa | 2943 |

<210> SEQ ID NO 2
<211> LENGTH: 2094
<212> TYPE: DNA
<213> ORGANISM: Streptococcus pneumoniae strain CGSP14

<400> SEQUENCE: 2

| | |
|---|---|
| atgaataaaa gaggtcttta ttcaaaacta ggaatttctg ttgtaggcat tagtctttta | 60 |
| atgggagttc ccactttgat tcatgcgaat gaattaaact atggtcaact gtccatatct | 120 |
| cctattttc aaggaggttc atatcaactg aacaataaga gtatagatat cagctctttg | 180 |
| ttattagata aattgtctgg agagagtcag acagtagtaa tgaaatttaa agcagataaa | 240 |
| ccaaactctc ttcaagcttt gtttggccta tctaatagta aagcaggctt taaaaataat | 300 |
| tactttcaa ttttcatgag agattctggt gagataggtg tagaaataag agacgcccaa | 360 |
| aagggaataa attatttatt ttctagacca gcttcattat ggggaaagca taaaggacag | 420 |
| gcagttgaaa atacactagt atttgtatct gattctaaag ataaaacata cacaatgtat | 480 |
| gttaatggaa tagaagtgtt ctctgaaaca gttgatacat ttttgccaat ttcaaatata | 540 |
| aatggtatag ataaggcaac actaggagct gttaatcgtg aaggcaagga acattacctc | 600 |
| gcaaaggaa gtattgatga atcagtcta tttaacaaag caattagtga tcaggaagtt | 660 |
| tcaaatattc ccttgtcaaa tccatttcag ttaatttttcc aatcaggaga ttctactcaa | 720 |
| gctaactatt ttagaatacc gacactatat acattaagta gtggaagagt tctatcaagt | 780 |
| attgatgcac gttatggtgg gactcatgat tctaaaagta agattaatat tgccacttct | 840 |
| tatagtgatg ataatgggaa aacgtggagt gagccaattt ttgctatgaa gtttaatgac | 900 |
| tatgaggagc agttagttta ctggccacga gataataaat taagaatag tcaaattagt | 960 |
| ggaagtgctt cattcataga ttcatccatt gttgaagata aaaatctgg aaaacgata | 1020 |
| ttactagctg atgttatgcc tgcgggtatt ggaaataata atgcaaataa agccgactca | 1080 |
| ggttttaaag aaataaatgg tcattattat ttaaaactaa agaagaatgg agataacgat | 1140 |
| ttccgttata cagttagaga aaatggtgtc gtttatgatg aaacaactaa taacctaca | 1200 |

```
aattatacta taaatgataa gtatgaagtt ttggagggag gaaagtctttt aacagtcgaa    1260 caatattcgg ttgattttga tagtggctct ttaagagaaa aacataatgg aaaacaggtc    1320
cctatgaatg ttttctacaa agattcgtta tttaaagtga ctcctactaa ttatatagca    1380
atgacaacta gtcagaatag aggagagagt tgggaacaat ttaagttgtt gcctccgttc    1440
ttaggagaaa aacataatgg aacttactta tgtcccggac aaggtttagc attaaaatca    1500
agtaacagat tgattttttgc aacatatact agtggagaac taacctatct catttctgat    1560
gatagtggtc aaacatggaa gaaatcctca gcttcaattc cgtttaaaaa tgcaacagca    1620
gaagcacaaa tggttgaact gagagatggt gtgattagaa cattctttag aaccactaca    1680
ggtaagatag cttatatgac tagtagagat tctggagaaa catggtcgga agtttcgtat    1740
attgatggaa tccaacaaac ttcatatggc acacaagtat ctgcaattaa atactctcaa    1800
ttaattgatg gaaaagaagc agtcattttg agtacaccaa attctagaag tggccgtaag    1860
ggaggtcaat tagttgtcgg tttagtcaat aaagaagatg atagtattga ttggaaatac    1920
cactatgata ttgatttgcc ttcgtatggt tatgcctatt ctgcgattac agaattgcca    1980
aatcatcaca taggtgtact gtttgaaaaa tatgattcgt ggtcgagaaa tgaattgcat    2040
ttaagcaatg tagttcagta tatagatttg gaaattaatg atttaacaaa ataa          2094

<210> SEQ ID NO 3
<211> LENGTH: 2223
<212> TYPE: DNA
<213> ORGANISM: Streptococcus pneumoniae strain CGSP14

<400> SEQUENCE: 3
atgaaaaaaa atattaaaca atacgtaacc ttaggtactg cagtggtatt atcagcattt      60
gttgctaact cagttgcagc tcaggagact gaaacttctg aagtatcaac accagagttg     120
gtgcaacctg ttgcaccaac gactccgatt tcggaagtac aacctaaatc gggtaactct     180
tcggaagtta ctgtacaacc tagaacagtc gaaactactg ttaaggatcc atcttctgca     240
acggaagaaa ctcctgtctt agaaaaaaat aatgttactt taacaggggg cggagaaaat     300
gttactaatg agttaaagga taaatttact agcggtgact ttactgtagt gattaagtac     360
aatcagtcta gtgagaaagg cttacaagct ctgtttggaa tatctaattc taaacccggt     420
caacaaaata gttatgtaga tgtgttcctt agagacaatg gtgaattggg aatggaagcg     480
cgtgatactt cttccaataa aaatcaccta gtatccagac ctgcttcagt ttggggtaag     540
tacaaacaag aagctgtgac taacactgtt gcagtagtag cagattcagt caaaaaaaca     600
tattctttat atgcaaatgg tacaaaagta gtagaaaaga agtggataaa cttcttaaac     660
atcaaggata ttaaaggtat tgattactat atgcttgggg gagtgaaacg tgcaggaaaa     720
acggcgtttg gttttaacgg aacactagaa aatatcaaat tctttaatag tgcattggat     780
gaagaaactg ttaaaaagat gacaacaaac gctgttactg acatttaatt ttatacggct     840
aatgatacaa caggttctaa ctatttccgt attccagttc tgtatacttt tagcaatggt     900
cgggtatttt caagcattga cgctcgttac ggcggaactc atgatttttt gaataaaatt     960
aatattgcta caagttatag tgatgataat ggtaagacat ggactaaacc aaaattaaca    1020
ttggcattcg atgattttgc gccagtacca ttagaatggc cttgtgatgt tggtggacgt    1080
gacttacaaa tcagcggtgg tgcaacctat attgactctg ttattgttga aaaaaataac    1140
aaacaagtac tcatgtttgc ggatgtgatg cctgctggag taagttttag agaagctact    1200
agaaaagatt caggttataa acaaattgat ggtaattatt accttaaatt aaagaaacaa    1260
```

-continued

```
ggtgatactg attacaatta tactattcgt gagaatggta ctgtatacga cgatcgtacc    1320
aacagaccaa ctgaattttc agtagataaa aatttcggta ttaaacaaaa tggtaattat    1380
ttgacagtag agcaatattc ggtttcattt aaaaataata aaaagactga atatcgtaat    1440
gggactcacg tccatatgaa tatcttctac aaagatgcat tgttcaaagt agtgccaacg    1500
aactatattg catatatttc tagcaatgat catggcgaat cttggtctgc accaacttta    1560
ttacctccta taatgggact taatcggaat gcgccttatt tgggtcctgg acgtggaatc    1620
attgaaagct caactggacg tattcttatt ccgtcttaca ctggtaaaga gtctgcattc    1680
atttatagtg acgataatgg agcatcttgg aaagttaaag ttgtgccact tccttctagt    1740
tggtcagcag aagcacaatt tgtagaattg agtccaggag taattcaagc atacatgcgt    1800
acaaataatg gtaaaattgc atatttaaca agtacagacg caggtactac ttggagtgca    1860
ccggaatatt tgaaatttgt ttcaaatcca agttatggaa cacaattatc aatcatcaat    1920
tatagtcaac tgattgatgg taaaaaggct gtcattttaa gtactccaaa ctccacaaat    1980
ggtcgtaaac acggacaaat ttggattggt ctaattaatg atgataatac aattgattgg    2040
cgttatcatc acgacgttga ttatagtaac tatggatact catattcaac attgacagag    2100
ttaccaaatc atgaaattgg attgatgttt gaaaaatttg attcatggtc tcgtaatgaa    2160
cttcatatga aaaatgttgt accatatata acatttaaga ttgaagatct gaaaagaat     2220 taa                                                                  2223
```

<210> SEQ ID NO 4
<211> LENGTH: 8241
<212> TYPE: DNA
<213> ORGANISM: Artificial Sequence
<220> FEATURE:
<223> OTHER INFORMATION: neuraminidase A (NanA), a sialidase A precursor, of Streptococcus pneumoniae strain CGSP14 with NCBI accession number NC_010582; Locus_Tag= SPCG_1665; protein ID= YP 001836382.1. This gene can be amplified by a primer set NanA-ATG-Kpn1 and NanA-TAA-Xho1.

<400> SEQUENCE: 4

```
ggtaccatgt cttatttcag aaatcgggat atagatatag agaggatcag tatgaatcgg     60
agtgttcaag aacgtaagtg tcgttatagc attaggaaac tatcggtagg agcggtttct    120
atgattgtag gagcagtggt atttggaacg tctcctgttt tagctcaaga aggggcaagt    180
gagcaacctc tggcaaatga aactcaactt tcggggagag ctcaaccct aactgataca    240 gaaaagagcc agccttcttc agagactgaa ctttctggca ataagcaaga acaagaaagg    300
aaagataagc aagaagaaaa aattccaaga gattactatg cacgagattt ggaaaatgtc    360
gaaacagtga tagaaaaaga agatgttgaa accaatgctt caaatggtca gagagttgat    420
ttatcaagtg aactagataa actaaagaaa cttgaaaacg caacagttca catggagttt    480
aagccagatg ccaaggcccc agcattctat aatctctttt ctgtgtcaag tgctactaaa    540
aaagatgagt acttcactat ggcagtttac aataatactg ctactctaga ggggcgtggt    600
tcggatgggc aacagtttta cggtaattac aacgatgcac ccttaaaagt taaaccaggt    660
cagtggaatt ctgtgacttt cacagttgaa aaaccgacga cagaactacc taaaggccga    720
gtgcgcctct acgtaaacgg ggtattatct cgaacaagtc tgaaatctgg caatttcatt    780
aaagatatgc cagatgtaac gcatgtgcaa atcggagcaa ccaagcgtgc caacaatacg    840
gtttgggggt caaatctaca gattcagaat ctcactgtgt ataatcgtgc tttaacacca    900
```

```
gaagaggtac aaaaacgtag tcaacttttt aaacgctcag atttagaaaa aaaactacct    960
gaaggagcgg ttttaacaga gaaaacggac atattcgaaa gcgggcgtaa cggtaaacca   1020
aataaagatg gaatcaagag ttatcgtatt ccagcacttc tcaagacaga taaaggaact   1080
ttgatcgcag gtgcagatga acgccgtctc cattcgagtg actggggtga tatcggtatg   1140
gtcatcagac gtagtgaaga taatggaaag acatggggag ataaggtggt tatctccaat   1200
cttcgagata atcctgaagc taaagatcct gctgcgccat cgcctctaaa tattgatatg   1260
gttttggttc aagacccgac aacaaagaga atcttctcaa tttatgatat gttcccagaa   1320
ggtcgagcag ttttttggaat gccaaaaaca cctgaaaaag cttatgaaaa gatgggggat   1380
aaaacttatc aaatcttgta taaacaagga gagtctggtc attatactgt tcgtgagaat   1440
ggagaagtgt ataatgcaca aaatcaaaag acgattatc gtgttgtagt gaatccaaca    1500
gaacctggct atagagataa aggaaatctt tacaaaggtc aggaattgat tggaaatatc   1560
tattttgcac acagtacaaa aaatccattt agagtagcca atacgagcta tctatggatg   1620
tcatatagtg acgatgatgg taaaacttgg tctgcaccga gagacattac tccaggtctt   1680
cgcaaggatt ggatgaagtt cctaggaaca ggtcctggaa caggaattgt acttcggaat   1740
gggcctcaca agggacggat tttgataccg gtttatacga ctaataatgt atctcactta   1800
aatggctcgc aatcttctcg tgtcatctat tcagatgatc atggaaaaac ttggcatgct   1860
ggagaagcgg tcaacgataa ccgtcaggta gacggtcaaa agatccactc ttctacgatg   1920
aacaatgaac gtgcgcaaaa tacagaatca acggtggtac aactaaacaa tggagatgtt   1980
aaactcttta tgcgtggttt gactggagat cttcaggttg ctacaagtaa agacggagga   2040
gtgacttggg agaaggatat caaacgttat ccacaggtta agatgtcta tgttcaaatg    2100
tctgctatcc atacgatgca cgaaggaaaa gaatacatca tcctcagtaa tgcaggtgga   2160
ccgaaacgtg aaaatgggat ggtccacttg gcacgtgtcg aagaaaatgg tgagttgact   2220
tggctcaaac acaatccaat tcaaaaagga gagtttgcct ataattcgct ccaagaatta   2280
ggaaatgggg agtatggtat cttgtatgaa catactgaaa aaggacaaaa tgcctatacc   2340
ctatcattta gaaaatttaa ttgggacttt ttgagcaaag atctgatttc tcctaccgaa   2400
gcgaaagtga agcgaactag agagatgggc aaaggagaga tgggcaaagg agttattggc   2460
ttggagttcg actcagaagt attggtcaac aaggctccaa cccttcaatt ggcaaatggt   2520
aaaacagcga ctttcctaac ccagtatgat agcaagacct tgttgtttgc agtagataag   2580
gaagatatcg gacaggaaat tattggtata gctaaaggaa gcatcgaaag tatgcataat   2640
cttcctgtaa atctagcagg tgccagagtt cctggcggag taaatggtag caaagcagcg   2700
gtgcatgaag ttccagaatt tacagggga gttaatggta cagagccagc tgttcatgaa    2760
atcgcagagt ataagggatc tgattcgctt gtaactctta ctacaaaaga agattatact   2820
tacaaagctc ctcttgctca gcaggcactt cctgaaacag gaaacaagga gagtgacctc   2880
ctagcttcac taggactaac agctttcttc cttggtctgt ttacgctagg gaaaaagaga   2940
gaacaactcg agcaccacca ccaccaccac tgagatccgg ctgctaacaa agcccgaaag   3000
gaagctgagt tggctgctgc caccgctgag caataactag cataacccct tggggcctct   3060
aaacgggtct tgagggggttt tttgctgaaa ggaggaacta tatccggatt ggcgaatggg   3120
acgcgccctg tagcggcgca ttaagcgcgg cgggtgtggt ggttacgcgc agcgtgaccg   3180
ctacacttgc cagcgcccta gcgcccgctc ctttcgcttt cttcccttcc tttctcgcca   3240
cgttcgccgg ctttccccgt caagctctaa atcggggggct cccttttaggg ttccgattta   3300
```

```
gtgctttacg gcacctcgac cccaaaaaac ttgattaggg tgatggttca cgtagtgggc   3360
catcgccctg atagacggtt tttcgccctt tgacgttgga gtccacgttc tttaatagtg   3420
gactcttgtt ccaaactgga acaacactca accctatctc ggtctattct tttgatttat   3480
aagggatttt gccgatttcg gcctattggt taaaaaatga gctgatttaa caaaaattta   3540
acgcgaattt taacaaaata ttaacgttta caatttcagg tggcacttt  cggggaaatg   3600 tgcgcggaac ccctatttgt ttattttct  aaatacattc aaatatgtat ccgctcatga   3660
attaattctt agaaaaactc atcgagcatc aaatgaaact gcaatttatt catatcagga   3720
ttatcaatac catatttttg aaaaagccgt ttctgtaatg aaggagaaaa ctcaccgagg   3780
cagttccata ggatggcaag atcctggtat cggtctgcga ttccgactcg tccaacatca   3840
atacaaccta ttaatttccc ctcgtcaaaa ataaggttat caagtgagaa atcaccatga   3900
gtgacgactg aatccggtga gaatggcaaa agtttatgca tttctttcca acttgttca    3960 acaggccagc cattacgctc gtcatcaaaa tcactcgcat caaccaaacc gttattcatt   4020
cgtgattgcg cctgagcgag acgaaatacg cgatcgctgt taaaaggaca attacaaaca   4080
ggaatcgaat gcaaccggcg caggaacact gccagcgcat caacaatatt ttcacctgaa   4140
tcaggatatt cttctaatac ctggaatgct gttttcccgg ggatcgcagt ggtgagtaac   4200
catgcatcat caggagtacg gataaaatgc ttgatggtcg gaagaggcat aaattccgtc   4260
agccagttta gtctgaccat ctcatctgta acatcattgg caacgctacc tttgccatgt   4320
ttcagaaaca actctggcgc atcgggcttc ccatacaatc gatagattgt cgcacctgat   4380
tgcccgacat tatcgcgagc ccatttatac ccatataaat cagcatccat gttggaattt   4440
aatcgcggcc tagagcaaga cgtttcccgt tgaatatggc tcataacacc ccttgtatta   4500
ctgtttatgt aagcagacag ttttattgtt catgaccaaa atcccttaac gtgagttttc   4560
gttccactga gcgtcagacc ccgtagaaaa gatcaaagga tcttcttgag atccttttt    4620 tctgcgcgta atctgctgct tgcaaacaaa aaaaccaccg ctaccagcgg tggtttgttt   4680
gccggatcaa gagctaccaa ctcttttcc  gaaggtaact ggcttcagca gagcgcagat   4740
accaaatact gtccttctag tgtagccgta gttaggccac cacttcaaga actctgtagc   4800
accgcctaca tacctcgctc tgctaatcct gttaccagtg gctgctgcca gtggcgataa   4860
gtcgtgtctt accgggttgg actcaagacg atagttaccg gataaggcgc agcggtcggg   4920
ctgaacgggg ggttcgtgca cacagcccag cttggagcga acgacctaca ccgaactgag   4980
atacctacag cgtgagctat gagaaagcgc cacgcttccc gaagggagaa aggcggacag   5040
gtatccggta agcggcaggg tcggaacagg agagcgcacg agggagcttc caggggggaaa  5100 cgcctggtat ctttatagtc ctgtcgggtt tcgccacctc tgacttgagc gtcgattttt   5160
gtgatgctcg tcagggggc  ggagcctatg gaaaaacgcc agcaacgcgg ccttttacg    5220 gttcctggcc ttttgctggc cttttgctca catgttcttt cctgcgttat ccctgattc    5280 tgtggataac cgtattaccg cctttgagtg agctgatacc gctcgccgca gccgaacgac   5340
cgagcgcagc gagtcagtga gcgaggaagc ggaagagcgc ctgatgcggt attttctcct   5400
tacgcatctg tgcggtattt cacaccgcat atatggtgca ctctcagtac aatctgctct   5460
gatgccgcat agttaagcca gtatacactc cgctatcgct acgtgactgg gtcatggctg   5520 cgcccccgaca cccgccaaca cccgctgacg cgccctgacg ggcttgtctg ctcccggcat   5580
ccgcttacag acaagctgtg accgtctccg ggagctgcat gtgtcagagg ttttcaccgt   5640
```

```
catcaccgaa acgcgcgagg cagctgcggt aaagctcatc agcgtggtcg tgaagcgatt    5700
cacagatgtc tgcctgttca tccgcgtcca gctcgttgag tttctccaga agcgttaatg    5760
tctggcttct gataaagcgg gccatgttaa gggcggtttt ttcctgtttg gtcactgatg    5820
cctccgtgta aggggatttt ctgttcatgg ggtaatgat accgatgaaa cgagagagga    5880
tgctcacgat acgggttact gatgatgaac atgcccggtt actggaacgt tgtgagggta    5940
aacaactggc ggtatggatg cggcgggacc agagaaaaat cactcagggt caatgccagc    6000
gcttcgttaa tacagatgta ggtgttccac agggtagcca gcagcatcct gcgatgcaga    6060
tccggaacat aatggtgcag ggcgctgact tccgcgtttc cagactttac gaaacacgga    6120
aaccgaagac cattcatgtt gttgctcagg tcgcagacgt tttgcagcag cagtcgcttc    6180
acgttcgctc gcgtatcggt gattcattct gctaaccagt aaggcaaccc cgccagccta    6240
gccgggtcct caacgacagg agcacgatca tgcgcacccg tggggccgcc atgccggcga    6300
taatggcctg cttctcgccg aaacgtttgg tggcgggacc agtgacgaag gcttgagcga    6360
gggcgtgcaa gattccgaat accgcaagcg acaggccgat catcgtcgcg ctccagcgaa    6420
agcggtcctc gccgaaaatg acccagagcg ctgccggcac ctgtcctacg agttgcatga    6480
taaagaagac agtcataagt gcggcgacga tagtcatgcc ccgcgcccac cggaaggagc    6540
tgactgggtt gaaggctctc aagggcatcg gtcgagatcc cggtgcctaa tgagtgagct    6600
aacttacatt aattgcgttg cgctcactgc ccgctttcca gtcgggaaac ctgtcgtgcc    6660
agctgcatta atgaatcggc caacgcgcgg ggagaggcgg tttgcgtatt gggcgccagg    6720
gtggtttttc ttttcaccag tgagacgggc aacagctgat tgcccttcac cgcctggccc    6780
tgagagagtt gcagcaagcg gtccacgctg gtttgcccca gcaggcgaaa atcctgtttg    6840
atggtggtta acggcgggat ataacatgag ctgtcttcgg tatcgtcgta tcccactacc    6900
gagatgtccg caccaacgcg cagcccggac tcggtaatgg cgcgcattgc gcccagcgcc    6960
atctgatcgt tggcaaccag catcgcagtg gaacgatgc cctcattcag catttgcatg    7020
gtttgttgaa aaccggacat ggcactccag tcgccttccc gttccgctat cggctgaatt    7080
tgattgcgag tgagatattt atgccagcca gccagacgca gacgcgccga gacagaactt    7140
aatgggcccg ctaacagcgc gatttgctgg tgacccaatg cgaccagatg ctccacgccc    7200
agtcgcgtac cgtcttcatg ggagaaaata atactgttga tgggtgtctg gtcagagaca    7260
tcaagaaata acgccggaac attagtgcag gcagcttcca cagcaatggc atcctggtca    7320
tccagcggat agttaatgat cagcccactg acgcgttgcg cgagaagatt gtgcaccgcc    7380
gctttacagg cttcgacgcc gcttcgttct accatcgaca ccaccacgct ggcacccagt    7440
tgatcggcgc gagatttaat cgccgcgaca atttgcgacg cgcgtgcag gccagactg    7500 gaggtggcaa cgccaatcag caacgactgt ttgcccgcca gttgttgtgc cacgcggttg    7560
ggaatgtaat tcagctccgc catcgccgct tccactttt cccgcgtttt cgcagaaacg    7620
tggctggcct ggttcaccac gcgggaaacg gtctgataag agacaccggc atactctgcg    7680
acatcgtata acgttactgg tttcacattc accaccctga attgactctc ttccgggcgc    7740
tatcatgcca taccgcgaaa ggttttgcgc cattcgatgg tgtccgggat ctcgacgctc    7800
tcccttatgc gactcctgca ttaggaagca gcccagtagt aggttgaggc cgttgagcac    7860
cgccgccgca aggaatggtg catgcaagga tggcgccc aacagtcccc ggccacggg    7920 gcctgccacc atacccacgc cgaaacaagc gctcatgagc ccgaagtggc gagcccgatc    7980
ttccccatcg gtgatgtcgg cgatataggc gccagcaacc gcacctgtgg cgccggtgat    8040
```

```
gccggccacg atgcgtccgg cgtagaggat cgagatcgat ctcgatcccg cgaaattaat    8100
acgactcact ataggggaat tgtgagcgga taacaattcc cctctagaaa taattttgtt    8160
taactttaag aaggagatat acatatgaaa gaaaccgctg ctgctaaatt cgaacgccag    8220
cacatggaca gcccagatct g                                              8241

<210> SEQ ID NO 5
<211> LENGTH: 7392
<212> TYPE: DNA
<213> ORGANISM: Streptococcus pneumoniae strain CGSP14

<400> SEQUENCE: 5
ggtaccatga ataaaagagg tctttattca aaactaggaa tttctgttgt aggcattagt      60
cttttaatgg gagttccac tttgattcat gcgaatgaat taaactatgg tcaactgtcc     120
atatctccta tttttcaagg aggttcatat caactgaaca ataagagtat agatatcagc     180
tctttgttat tagataaatt gtctggagag agtcagacag tagtaatgaa atttaaagca     240
gataaaccaa actctcttca agctttgttt ggcctatcta atagtaaagc aggctttaaa     300 ataattact tttcaatttt catgagagat tctggtgaga taggtgtaga ataagagac      360 gcccaaaagg gaataaatta tttattttct agaccagctt cattatgggg aaagcataaa     420
ggacaggcag ttgaaaatac actagtattt gtatctgatt ctaaagataa acatacaca     480 atgtatgtta atgaataga agtgttctct gaaacagttg atacattttt gccaatttca     540
aatataaatg gtatagataa ggcaacacta ggagctgtta atcgtgaagg caaggaacat     600
tacctcgcaa aaggaagtat tgatgaaatc agtctattta caaagcaat tagtgatcag     660 gaagtttcaa atattccctt gtcaaatcca tttcagttaa ttttccaatc aggagattct     720
actcaagcta actattttag aataccgaca ctatatacat taagtagtgg aagagttcta     780
tcaagtattg atgcacgtta tggtgggact catgattcta aaagtaagat taatattgcc     840
acttcttata gtgatgataa tgggaaaacg tggagtgagc caatttttgc tatgaagttt     900
aatgactatg aggagcagtt agtttactgg ccacgagata taaaattaaa gaatagtcaa     960
attagtggaa gtgcttcatt catagattca tccattgttg aagataaaaa atctgggaaa    1020
acgatattac tagctgatgt tatgcctgcg ggtattggaa ataataatgc aaataaagcc    1080
gactcaggtt ttaaagaaat aaatggtcat tattatttaa aactaaagaa gaatgggat    1140 aacgatttcc gttatacagt tagagaaaat ggtgtcgttt atgatgaaac aactaataaa    1200
cctacaaatt atactataaa tgataagtat gaagttttgg agggaggaaa gtctttaaca    1260
gtcgaacaat attcggttga ttttgatagt ggctctttaa gagaaaaaca taatggaaaa    1320
caggtcccta tgaatgtttt ctacaaagat tcgttattta agtgactcc tactaattat    1380 atagcaatga caactagtca gaatagagga gagagttggg aacaatttaa gttgttgcct    1440
ccgttcttag gagaaaaaca taatggaact tactatgtc ccggacaagg tttagcatta    1500
aaatcaagta acagattgat ttttgcaaca tatactagtg gagaactaac ctatctcatt    1560
tctgatgata gtggtcaaac atggaagaaa tcctcagctt caattccgtt taaaaatgca    1620
acagcagaag cacaaatggt tgaactgaga gatggtgtga ttagaacatt ctttagaacc    1680
actacaggta agatagctta tatgactagt agagattctg gagaaacatg gtcggaagtt    1740
tcgtatattg atggaatcca acaaacttca tatggcacac aagtatctgc aattaaatac    1800
tctcaattaa ttgatggaaa agaagcagtc attttgagta caccaaattc tagaagtggc    1860
```

```
cgtaagggag gtcaattagt tgtcggttta gtcaataaag aagatgatag tattgattgg    1920
aaataccact atgatattga tttgccttcg tatggttatg cctattctgc gattacagaa    1980
ttgccaaatc atcacatagg tgtactgttt gaaaaatatg attcgtggtc gagaaatgaa    2040
ttgcatttaa gcaatgtagt tcagtatata gatttggaaa ttaatgattt aacaaaactc    2100
gagcaccacc accaccacca ctgagatccg gctgctaaca aagcccgaaa ggaagctgag    2160
ttggctgctg ccaccgctga gcaataacta gcataacccc ttggggcctc taaacgggtc    2220
ttgaggggtt ttttgctgaa aggaggaact atatccggat tggcgaatgg gacgcgccct    2280
gtagcggcgc attaagcgcg gcgggtgtgg tggttacgcg cagcgtgacc gctacacttg    2340
ccagcgccct agcgcccgct cctttcgctt tcttcccttc ctttctcgcc acgttcgccg    2400
gctttccccg tcaagctcta aatcgggggc tccctttagg gttccgattt agtgctttac    2460
ggcacctcga ccccaaaaaa cttgattagg gtgatggttc acgtagtggg ccatcgccct    2520
gatagacggt ttttcgccct tgacgttgg agtccacgtt ctttaatagt ggactcttgt    2580
tccaaactgg aacaacactc aaccctatct cggtctattc ttttgattta agggatttt    2640 tgccgatttc ggcctattgg ttaaaaaatg agctgattta caaaaatttt aacgcgaatt    2700
ttaacaaaat attaacgttt acaatttcag gtggcacttt tcggggaaat gtgcgcggaa    2760
cccctatttg tttatttttc taaatacatt caaatatgta tccgctcatg aattaattct    2820
tagaaaaact catcgagcat caaatgaaac tgcaatttat tcatatcagg attatcaata    2880
ccatattttt gaaaaagccg tttctgtaat gaaggagaaa actcaccgag gcagttccat    2940
aggatggcaa gatcctggta tcggtctgcg attccgactc gtccaacatc aatacaacct    3000
attaatttcc cctcgtcaaa aataaggtta tcaagtgaga aatcaccatg agtgacgact    3060
gaatccggtg agaatggcaa aagtttatgc atttctttcc agacttgttc aacaggccag    3120
ccattacgct cgtcatcaaa atcactcgca tcaaccaaac cgttattcat tcgtgattgc    3180
gcctgagcga cgaaatac gcgatcgctg ttaaaaggac aattacaaac aggaatcgaa    3240
tgcaaccggc gcaggaacac tgccagcgca tcaacaatat tttcacctga atcaggatat    3300
tcttctaata cctggaatgc tgttttcccg gggatcgcag tggtgagtaa ccatgcatca    3360
tcaggagtac ggataaaatg cttgatggtc ggaagaggca taaattccgt cagccagttt    3420
agtctgacca tctcatctgt aacatcattg gcaacgctac ctttgccatg tttcagaaac    3480
aactctggcg catcgggctt cccatacaat cgatagattg tcgcacctga ttgcccgaca    3540
ttatcgcgag cccatttata cccatataaa tcagcatcca tgttggaatt taatcgcggc    3600
ctagagcaag acgtttcccg ttgaatatgg ctcataacac cccttgtatt actgtttatg    3660
taagcagaca gttttattgt tcatgaccaa aatcccttaa cgtgagtttt cgttccactg    3720
agcgtcagac cccgtagaaa agatcaaagg atcttcttga gatccttttt ttctgcgcgt    3780
aatctgctgc ttgcaaacaa aaaaaccacc gctaccagcg gtggtttgtt tgccggatca    3840
agagctacca actctttttc cgaaggtaac tggcttcagc agagcgcaga taccaaatac    3900
tgtccttcta gtgtagccgt agttaggcca ccacttcaag aactctgtag caccgcctac    3960
atacctcgct ctgctaatcc tgttaccagt ggctgctgcc agtggcgata agtcgtgtct    4020
taccgggttg gactcaagac gatagttacc ggataaggcg cagcggtcgg gctgaacggg    4080
gggttcgtgc acacagccca gcttggagcg aacgacctac accgaactga gatacctaca    4140
gcgtgagcta tgagaaagcg ccacgcttcc cgaagggaga aaggcggaca ggtatccggt    4200
aagcggcagg gtcggaacag gagagcgcac gagggagctt ccaggggaa acgcctggta    4260
```

```
tctttatagt cctgtcgggt ttcgccacct ctgacttgag cgtcgatttt tgtgatgctc   4320
gtcagggggg cggagcctat ggaaaaacgc cagcaacgcg gccttttac ggttcctggc    4380 cttttgctgg cctttgctc acatgttctt tcctgcgtta tccctgatt ctgtggataa    4440 ccgtattacc gcctttgagt gagctgatac cgctcgccgc agccaacga ccagcgcag    4500 cgagtcagtg agcgaggaag cggaagagcg cctgatgcgg tattttctcc ttacgcatct   4560
gtgcggtatt tcacaccgca tatatggtgc actctcagta caatctgctc tgatgccgca   4620
tagttaagcc agtatacact ccgctatcgc tacgtgactg ggtcatggct gcgccccgac   4680
acccgccaac acccgctgac gcgccctgac gggcttgtct gctcccggca tccgcttaca   4740
gacaagctgt gaccgtctcc gggagctgca tgtgtcagag gttttcaccg tcatcaccga   4800
aacgcgcgag gcagctgcgg taaagctcat cagcgtggtc gtgaagcgat tcacagatgt   4860
ctgcctgttc atccgcgtcc agctcgttga gtttctccag aagcgttaat gtctggcttc   4920
tgataaagcg ggccatgtta agggcggttt tttcctgttt ggtcactgat gcctccgtgt   4980 aaggggggatt tctgttcatg ggggtaatga taccgatgaa acgagagagg atgctcacga   5040
tacgggttac tgatgatgaa catgcccggt tactggaacg ttgtgagggt aaacaactgg   5100
cggtatggat gcggcgggac cagagaaaaa tcactcaggg tcaatgccag cgcttcgtta   5160
atacagatgt aggtgttcca cagggtagcc agcagcatcc tgcgatgcag atccggaaca   5220
taatggtgca gggcgctgac ttccgcgttt ccagacttta cgaaacacgg aaaccgaaga   5280
ccattcatgt tgttgctcag gtcgcagacg ttttgcagca gcagtcgctt cacgttcgct   5340
cgcgtatcgg tgattcattc tgctaaccag taaggcaacc ccgccagcct agccgggtcc   5400
tcaacgacag gagcacgatc atgcgcaccc gtggggccgc catgccggcg ataatggcct   5460
gcttctcgcc gaaacgtttg gtggcgggac cagtgacgaa ggcttgagcg agggcgtgca   5520
agattccgaa taccgcaagc gacaggccga tcatcgtcgc gctccagcga aagcggtcct   5580
cgccgaaaat gacccagagc gctgccggca cctgtcctac gagttgcatg ataaagaaga   5640
cagtcataag tgcggcgacg atagtcatgc cccgcgccca ccggaaggag ctgactgggt   5700
tgaaggctct caagggcatc ggtcgagatc ccggtgccta atgagtgagc taacttacat   5760
taattgcgtt gcgctcactg cccgctttcc agtcgggaaa cctgtcgtgc cagctgcatt   5820
aatgaatcgg ccaacgcgcg gggagaggcg gtttgcgtat tgggcgccag ggtggttttt   5880
cttttcacca gtgagacggg caacagctga ttgcccttca ccgcctggcc ctgagagagt   5940
tgcagcaagc ggtccacgct ggtttgcccc agcaggcgaa aatcctgttt gatggtggtt   6000
aacggcggga taaacatga gctgtcttcg gtatcgtcgt atcccactac cgagatgtcc   6060
gcaccaacgc gcagcccgga ctcggtaatg gcgcgcattg cgcccagcgc catctgatcg   6120
ttggcaacca gcatcgcagt gggaacgatg ccctcattca gcatttgcat ggtttgttga   6180
aaaccggaca tggcactcca gtcgccttcc cgttccgcta tcggctgaat ttgattgcga   6240
gtgagatatt tatgccagcc agccagacgc agacgcgccg agacagaact taatgggccc   6300
gctaacagcg cgatttgctg gtgacccaat gcgaccagat gctccacgcc cagtcgcgta   6360
ccgtcttcat gggagaaaat aatactgttg atgggtgtct ggtcagagac atcaagaaat   6420
aacgccggaa cattagtgca ggcagcttcc acagcaatgg catcctggtc atccagcgga   6480
tagttaatga tcagcccact gacgcgttgc gcgagaagat tgtgcaccgc cgctttacag   6540
gcttcgacgc cgcttcgttc taccatcgac accaccacgc tggcacccag ttgatcggcg   6600
```

```
cgagatttaa tcgccgcgac aatttgcgac ggcgcgtgca gggccagact ggaggtggca    6660
acgccaatca gcaacgactg tttgcccgcc agttgttgtg ccacgcggtt gggaatgtaa    6720
ttcagctccg ccatcgccgc ttccactttt tcccgcgttt tcgcagaaac gtggctggcc    6780
tggttcacca cgcgggaaac ggtctgataa gagacaccgg catactctgc gacatcgtat    6840
aacgttactg gtttcacatt caccaccctg aattgactct cttccgggcg ctatcatgcc    6900
ataccgcgaa aggttttgcg ccattcgatg gtgtccggga tctcgacgct ctcccttatg    6960
cgactcctgc attaggaagc agcccagtag taggttgagg ccgttgagca ccgccgccgc    7020
aaggaatggt gcatgcaagg agatggcgcc caacagtccc ccggccacgg ggcctgccac    7080
catacccacg ccgaaacaag cgctcatgag cccgaagtgg cgagcccgat cttccccatc    7140
ggtgatgtcg gcgatatagg cgccagcaac cgcacctgtg gcgccggtga tgccggccac    7200
gatgcgtccg gcgtagagga tcgagatcga tctcgatccc gcgaaattaa tacgactcac    7260
tatagggaa ttgtgagcgg ataacaattc ccctctagaa ataattttgt ttaactttaa    7320
gaaggagata tacatatgaa agaaaccgct gctgctaaat tcgaacgcca gcacatggac    7380
agcccagatc tg                                                        7392

<210> SEQ ID NO 6
<211> LENGTH: 7521
<212> TYPE: DNA
<213> ORGANISM: Streptococcus pneumoniae strain CGSP14

<400> SEQUENCE: 6
ggtaccatga aaaaaaatat taaacaatac gtaaccttag gtactgcagt ggtattatca      60
gcatttgttg ctaactcagt tgcagctcag gagactgaaa cttctgaagt atcaacacca     120
gagttggtgc aacctgttgc accaacgact ccgatttcgg aagtacaacc taaatcgggt     180
aactcttcgg aagttactgt acaacctaga acagtcgaaa ctactgttaa ggatccatct     240
tctgcaacgg aagaaactcc tgtcttagaa aaaaataatg ttactttaac aggggcgga     300
gaaaatgtta ctaatgagtt aaaggataaa tttactagcg gtgactttac tgtagtgatt     360
aagtacaatc agtctagtga gaaaggctta caagctctgt ttggaatatc taattctaaa     420
cccggtcaac aaaatagtta tgtagatgtg ttccttagag acaatggtga attgggaatg     480
gaagcgcgtg atacttcttc caataaaaat cacctagtat ccagacctgc ttcagtttgg     540
ggtaagtaca acaagaagc tgtgactaac actgttgcag tagtagcaga ttcagtcaaa     600
aaaacatatt ctttatatgc aaatggtaca aagtagtag aaaagaaagt ggataacttc     660
ttaaacatca aggatattaa aggtattgat tactatatgc ttgggggagt gaaacgtgca     720
ggaaaaacgg cgtttggttt taacggaaca ctagaaaaata tcaaattctt taatagtgca     780
ttggatgaag aaactgttaa aaagatgaca acaaacgctg ttactggaca tttaatttat     840
acggctaatg atacaacagg ttctaactat ttccgtattc cagttctgta actttttagc     900
aatggtcggg tattttcaag cattgacgct cgttacggcg gaactcatga ttttttgaat     960
aaaattaata ttgctacaag ttatagtgat gataatggta agacatggac taaaccaaaa    1020
ttaacattgg cattcgatga ttttgcgcca gtaccattag aatggccttg tgatgttggt    1080
ggacgtgact tacaaatcag cggtggtgca acctatattg actctgttat tgttgaaaaa    1140
aataacaaac aagtactcat gtttgcggat gtgatgcctg ctggagtaag ttttagagaa    1200
gctactagaa aagattcagg ttataaacaa attgatggta attattacct taaattaaag    1260
aaacaaggtg atactgatta caattatact attcgtgaga atggtactgt atacgacgat    1320
```

```
cgtaccaaca gaccaactga attttcagta gataaaaatt tcggtattaa acaaaatggt    1380
aattatttga cagtagagca atattcggtt tcatttaaaa ataataaaaa gactgaatat    1440
cgtaatggga ctcacgtcca tatgaatatc ttctacaaag atgcattgtt caaagtagtg    1500
ccaacgaact atattgcata tatttctagc aatgatcatg gcgaatcttg gtctgcacca    1560
actttattac ctcctataat gggacttaat cggaatgcgc cttatttggg tcctggacgt    1620
ggaatcattg aaagctcaac tggacgtatt cttattccgt cttacactgg taaagagtct    1680
gcattcattt atagtgacga taatggagca tcttggaaag ttaaagttgt gccacttcct    1740
tctagttggt cagcagaagc acaatttgta gaattgagtc caggagtaat tcaagcatac    1800
atgcgtacaa ataatggtaa aattgcatat ttaacaagta cagacgcagg tactacttgg    1860
agtgcaccgg aatatttgaa atttgtttca aatccaagtt atggaacaca attatcaatc    1920
atcaattata gtcaactgat tgatggtaaa aaggctgtca ttttaagtac tccaaactcc    1980
acaaatggtc gtaaacacgg acaaatttgg attggtctaa ttaatgatga taatacaatt    2040
gattggcgtt atcatcacga cgttgattat agtaactatg gatactcata ttcaacattg    2100
acagagttac caaatcatga aattggattg atgtttgaaa aatttgattc atggtctcgt    2160
aatgaacttc atatgaaaaa tgttgtacca tatataacat ttaagattga agatctgaaa    2220
aagaatctcg agcaccacca ccaccaccac tgagatccgg ctgctaacaa agcccgaaag    2280
gaagctgagt tggctgctgc caccgctgag caataactag cataaccect tggggcctct    2340 aaacgggtct tgaggggttt tttgctgaaa ggaggaacta tatccggatt ggcgaatggg    2400
acgcgccctg tagcggcgca ttaagcgcgg cgggtgtggt ggttacgcgc agcgtgaccg    2460
ctacacttgc cagcgcccta gcgcccgctc ctttcgcttt cttcccttcc tttctcgcca    2520
cgttcgccgg ctttccccgt caagctctaa atcgggggct cccttagggg ttccgattta    2580
gtgctttacg gcacctcgac cccaaaaaac ttgattaggg tgatggttca cgtagtgggc    2640
catcgccctg atagacggtt tttcgccctt tgacgttgga gtccacgttc tttaatagtg    2700
gactcttgtt ccaaactgga acaacactca accctatctc ggtctattct tttgatttat    2760
aagggatttt gccgatttcg gcctattggt taaaaaatga gctgatttaa caaaaattta    2820
acgcgaattt taacaaaata ttaacgttta caatttcagg tggcactttt cggggaaatg    2880
tgcgcggaac ccctatttgt ttattttct aaatacattc aaatatgtat ccgctcatga    2940
attaattctt agaaaaactc atcgagcatc aaatgaaact gcaatttatt catatcagga    3000
ttatcaatac catattttg aaaaagccgt ttctgtaatg aaggagaaaa ctcaccgagg    3060
cagttccata ggatggcaag atcctggtat cggtctgcga ttccgactcg tccaacatca    3120
atacaaccta ttaatttccc ctcgtcaaaa ataaggttat caagtgagaa atcaccatga    3180
gtgacgactg aatccggtga gaatggcaaa agtttatgca tttctttcca gacttgttca    3240
acaggccagc cattacgctc gtcatcaaaa tcactcgcat caaccaaacc gttattcatt    3300
cgtgattgcg cctgagcgag acgaaatacg cgatcgctgt taaaaggaca attacaaaca    3360
ggaatcgaat gcaaccggcg caggaacact gccagcgcat caacaatatt ttcacctgaa    3420
tcaggatatt cttctaatac ctggaatgct gttttcccgg ggatcgcagt ggtgagtaac    3480
catgcatcat caggagtacg gataaaatgc ttgatggtcg aagaggcat aaattccgtc    3540 agccagttta gtctgaccat ctcatctgta acatcattgg caacgctacc tttgccatgt    3600
ttcagaaaca actctggcgc atcgggcttc ccatacaatc gatagattgt cgcacctgat    3660
```

```
tgcccgacat tatcgcgagc ccatttatac ccatataaat cagcatccat gttggaattt    3720
aatcgcggcc tagagcaaga cgtttcccgt tgaatatggc tcataacacc ccttgtatta    3780
ctgtttatgt aagcagacag ttttattgtt catgaccaaa atcccttaac gtgagttttc    3840
gttccactga cgtcagacc ccgtagaaaa gatcaaagga tcttcttgag atccttttt     3900 tctgcgcgta atctgctgct tgcaaacaaa aaaaccaccg ctaccagcgg tggtttgttt    3960
gccggatcaa gagctaccaa ctcttttttcc gaaggtaact ggcttcagca gagcgcagat    4020
accaaatact gtccttctag tgtagccgta gttaggccac cacttcaaga actctgtagc    4080
accgcctaca tacctcgctc tgctaatcct gttaccagtg ctgctgcca gtggcgataa     4140 gtcgtgtctt accgggttgg actcaagacg atagttaccg gataaggcgc agcggtcggg    4200
ctgaacgggg ggttcgtgca cacagcccag cttggagcga acgacctaca ccgaactgag    4260
atacctacag cgtgagctat gagaaagcgc cacgcttccc gaagggagaa aggcggacag    4320
gtatccggta gcggcaggg tcggaacagg agagcgcacg agggagcttc caggggggaaa    4380 cgcctggtat ctttatagtc ctgtcgggtt tcgccacctc tgacttgagc gtcgattttt    4440
gtgatgctcg tcagggggc ggagcctatg gaaaaacgcc agcaacgcgg cctttttacg     4500
gttcctggcc ttttgctggc cttttgctca catgttcttt cctgcgttat cccctgattc    4560
tgtggataac cgtattaccg cctttgagtg agctgatacc gctcgccgca gccgaacgac    4620
cgagcgcagc gagtcagtga gcgaggaagc ggaagagcgc ctgatgcggt attttctcct    4680
tacgcatctg tgcggtattt cacaccgcat atatggtgca ctctcagtac aatctgctct    4740
gatgccgcat agttaagcca gtatacactc cgctatcgct acgtgactgg gtcatggctg    4800
cgccccgaca cccgccaaca cccgctgacg cgccctgacg ggcttgtctg ctcccggcat    4860
ccgcttacag acaagctgtg accgtctccg ggagctgcat gtgtcagagg ttttcaccgt    4920
catcaccgaa acgcgcgagg cagctgcggt aaagctcatc agcgtggtcg tgaagcgatt    4980
cacagatgtc tgcctgttca tccgcgtcca gctcgttgag tttctccaga agcgttaatg    5040
tctggcttct gataaagcgg gccatgttaa gggcggtttt ttcctgtttg gtcactgatg    5100
cctccgtgta aggggatttt ctgttcatgg ggtaatgat accgatgaaa cgagagagga    5160
tgctcacgat acgggttact gatgatgaac atgcccggtt actggaacgt tgtgagggta    5220
aacaactggc ggtatggatg cggcgggacc agagaaaaat cactcagggt caatgccagc    5280
gcttcgttaa tacagatgta ggtgttccac agggtagcca gcagcatcct gcgatgcaga    5340 tccgaacat aatggtgcag ggcgctgact tccgcgtttc cagactttac gaaacacgga    5400
aaccgaagac cattcatgtt gttgctcagg tcgcagacgt tttgcagcag cagtcgcttc    5460
acgttcgctc gcgtatcggt gattcattct gctaaccagt aaggcaaccc cgccagccta    5520
gccgggtcct caacgacagg agcacgatca tgcgcacccg tggggccgcc atgccggcga    5580
taatggcctg cttctcgccg aaacgtttgg tggcgggacc agtgacgaag gcttgagcga    5640
gggcgtgcaa gattccgaat accgcaagcg acaggccgat catcgtcgcg ctccagcgaa    5700
agcggtcctc gccgaaaatg acccagagcg ctgccggcac ctgtcctacg agttgcatga    5760
taaagaagac agtcataagt gcggcgacga tagtcatgcc ccgcgcccac cggaaggagc    5820
tgactgggtt gaaggctctc aagggcatcg gtcgagatcc cggtgcctaa tgagtgagct    5880
aacttacatt aattgcgttg cgctcactgc ccgctttcca gtcgggaaac ctgtcgtgcc    5940
agctgcatta atgaatcggc caacgcgcgg ggagaggcgg tttgcgtatt gggcgccagg    6000 gtggttttc ttttcaccag tgagacgggc aacagctgat tgcccttcac cgcctggccc    6060
```

-continued

```
tgagagagtt gcagcaagcg gtccacgctg gtttgccca gcaggcgaaa atcctgtttg    6120
atggtggtta acggcgggat ataacatgag ctgtcttcgg tatcgtcgta tcccactacc   6180
gagatgtccg caccaacgcg cagcccggac tcggtaatgg cgcgcattgc gcccagcgcc   6240
atctgatcgt tggcaaccag catcgcagtg ggaacgatgc cctcattcag catttgcatg   6300
gtttgttgaa aaccggacat ggcactccag tcgccttccc gttccgctat cggctgaatt   6360
tgattgcgag tgagatattt atgccagcca gccagacgca gacgcgccga gacagaactt   6420
aatgggcccg ctaacagcgc gatttgctgg tgacccaatg cgaccagatg ctccacgccc   6480
agtcgcgtac cgtcttcatg ggagaaaata atactgttga tgggtgtctg gtcagagaca   6540
tcaagaaata acgccggaac attagtgcag gcagcttcca cagcaatggc atcctggtca   6600
tccagcggat agttaatgat cagcccactg acgcgttgcg cgagaagatt gtgcaccgcc   6660
gctttacagg cttcgacgcc gcttcgttct accatcgaca ccaccacgct ggcacccagt   6720
tgatcggcgc gagatttaat cgccgcgaca atttgcgacg gcgcgtgcag ggccagactg   6780
gaggtggcaa cgccaatcag caacgactgt ttgcccgcca gttgttgtgc cacgcggttg   6840
ggaatgtaat tcagctccgc catcgccgct tccacttttt cccgcgtttt cgcagaaacg   6900
tggctggcct ggttcaccac gcgggaaacg gtctgataag agacaccggc atactctgcg   6960
acatcgtata acgttactgg tttcacattc accaccctga attgactctc ttccgggcgc   7020
tatcatgcca taccgcgaaa ggttttgcgc cattcgatgg tgtccgggat ctcgacgctc   7080
tcccttatgc gactcctgca ttaggaagca gcccagtagt aggttgaggc cgttgagcac   7140
cgccgccgca aggaatggtg catgcaagga gatgcgccc aacagtcccc cggccacggg   7200
gcctgccacc atacccacgc cgaaacaagc gctcatgagc ccgaagtggc gagcccgatc   7260
ttccccatcg gtgatgtcgg cgatataggc gccagcaacc gcacctgtgg cgccggtgat   7320
gccggccacg atgcgtccgg cgtagaggat cgagatcgat ctcgatcccg cgaaattaat   7380
acgactcact atagggaat tgtgagcgga taacaattcc cctctagaaa taattttgtt    7440
taactttaag aaggagatat acatatgaaa gaaaccgctg ctgctaaatt cgaacgccag   7500
cacatggaca gcccagatct g                                             7521
```

METHOD OF DETECTING THE PRESENCE OF PNEUMOCOCCAL NEURAMINIDASES IN *STREPTOCOCCUS PNEUMONIAE*-INFECTED SAMPLES

This application is a divisional application of application Ser. No. 13/244,482, filed on Sep. 25, 2011, the entire contents of which are incorporated by reference.

FIELD OF THE INVENTION

The present invention relates to the development of vaccine for preventing pneumococcal diseases, and to the diagnosis of the pneumococci-infected samples not just from urine but also from blood and pleural effusion in pyothorax. More particularly, this invention relates to a universal protein vaccine against the pneumococcal infection.

BACKGROUND OF THE INVENTION

*Streptococcus pneumoniae* is one of Gram-positive encapsulated diplococci. Pneumococcal infection is a leading infectious cause of the high mortality and morbidity worldwide, especially among young children below two years of age and the elderly over sixty years of age. Globally, pneumococcal infection has been estimated to cause about 1.6 million deaths annually, including 1 million children less than five years old. Even though certain vaccines have been applied to prevent the *S. pneumoniae* infection, the mortality rate caused by this organism is still ranked the highest. The spectrum of the *S. pneumoniae*-related diseases includes invasive pneumococcal disease (IPD), such as sepsis and meningitis; lower respiratory infections, such as bacterial pneumonia; and upper respiratory infections, such as acute otitis media (AOM) (Tuomanen et al., 1995).

According to the reports of World Health Organization (WHO) in 2005, acute respiratory tract infections were the major cause of death globally, in which the deaths were chiefly attributable to the *S. pneumoniae*-associated community-acquired pneumonia (CAP). This threatening issue strongly raises the urgency for both diagnosis and prevention. Although the diagnoses of pneumococci have been developed for decades, we still heavily rely on conventional culture methods that are tedious and time-consuming, to proliferate enough bacteria for specific and sensitive detection. Therefore, based on specific DNA amplification and antigen detection, the tests of non-culture samples from sputum, urine, and blood have been continuously developed over time in order to identify pneumococci as the etiological agent of diseases. However, the consequences of those tests were always unsatisfactory in certain applications. For instance, the application of PCR testing for the diagnosis of IPD has ever shown to be insufficiently sensitive when using blood or urinary samples, and poorly specific when using respiratory samples. To overcome the problem of poor specificity when using sputum samples, recently a dual-PCR testing protocol using pneumococcal lytA and ply as targets has been successfully developed and evaluated.

Another disappointing aspect for diagnosis revealed that only one third of pathogens could be recovered from patient's sputum when using conventional culture methods. In addition, the controversial results lack specificity correlated to CAP because nasopharyngeal carriage of pneumococci could also be found in both healthy individuals and inadequate sputum samples. In addition, the etiological pathogens of CAP tested from blood culture and pleural fluid were specific, but the positive rates were lower (<30%) compared to that from sputum sample. For this reason, the development of antigen detection was applied to compensate the drawback of low specificity. Higher sensitivity of the pleural test compared to pleural cultures indicated that antigen detection for pleural samples rather than pleural culture could be a better application for the CAP study of pneumococcal etiology. Also, the detection of BinaxNOW pneumococcal C-polysaccharide in a urine sample with CAP shows unsatisfied result due to its high rate of false positive.

Currently, there are two kinds of vaccines, 23-valent pneumococcal polysaccharide vaccine (PPV23) and 7-valent pneumococcal conjugate vaccine (PCV7), available for general protection against potential IPD-causative pathogen strains. Vaccine PCV7 can target seven serotypes, including 4, 6B, 9V, 14, 18C, 19F, and 23F. Before the introduction of PCV7, the PCV7-targeted 7 serotypes (4, 6B, 9V, 14, 18C, 19F, and 23F) were responsible for about 90% of incidence of IPD in young children in the United States and for more than 60% of those in Europe. After PCV7 vaccination, the cases of IPD in children less than 5 years old declined by 56% in 2001 and by 76% in 2004. In contrast, PPV23 vaccination seems to difficultly reach firm conclusions in clinical effectiveness (around 50-70% effective). Although two doses of PCV7 and following one dose of PPV23 were recommended to broaden protection, the effectiveness of vaccines was significant on the protection of those seven PCV7-covered serotypes rather than others. The results suggested that PPV23 seems not necessary as a boost dose for broadening protection.

At least 93 different polysaccharide (PS) capsules of *S. pneumoniae* have been verified to be specific serotypes, and further classified to be 46 serogroups. Among all pathogenic pneumoncocci worldwide, serotype 14 and serogroup 6 are predominant. In addition, the majority of IPD is generally caused by about 15 serotypes. However, only a few antimicrobial resistant pneumococcal clones could spread fast. The incidence of antimicrobial resistance of pneumococci varies regionally, and is associated with the spectrum of antibiotic use, population density, the indigenous prevalence of resistant strains, ages and time. Although the resistance patterns have been shown to be different around the world, the predominant serotypes commonly identified are 6A/B, 9V, 14, 19A/F, and 23F. Based on epidemiological study, the nasopharyngeal (NP) carriage of predominant pneumococci has been observed in many young children, indicating that NP carriage may play an important role in pneumococcal transmission, especially for antibiotic-resistant strains.

Despite effective reduction of the incidence of IPD caused by vaccine serotypes in both children and adults due to the usage of the current pneumococcal vaccine PCV7, the mortality rate of pneumococcal disease remains high. After the introduction of PCV7 in 2000, nonvaccine serotype 3 was found to be a significant cause for necrotizing pneumonia in children in Utah, whereas a mucoid serotype 3 was usually reported to cause lung abscess in adults. Serotype 19A has been reported the predominant serotype causing IPD all over the world. In Taiwan, complicated pneumococcal pneumonia still remains a clinically intricate problem, and its significant association with the clonal spread of CC320 within serotype 19A was noteworthy recently in Taiwan. Besides pneumococcal serotypes 3 and 19A, other nonvaccine serotypes, including 1, 5, 6A, and 7F, were also common causes for IPD around the world (Grijalva and Pelton, 2011). A second-generation 13-valent pneumococcal conjugate vaccine (PCV13) was therefore developed to address this new global issue of pneumococcal infection in 2010 (Grijalva and Pelton, 2011).

Hemolytic uremic syndrome (HUS), one of the most severe complications of IPD, mainly occurs in children, and it is also associated with hemolytic anemia, thrombocytopenia, and acute renal failure. This disorder, usually occurring in healthy young children, is one of the most common causes of acute renal failure in pediatric patients. Management of the pneumococcal HUS primarily includes an intensive antimicrobial therapy and the dialysis and transfusion of washed RBC, platelets and plasma. Most cases of HUS are reported by an acute gastroenteritis related to *Escherichia coli* (O157: H7), and often show good prognosis with recovery of renal function. However, the mortality rate of patients with pneumococcal HUS was high in early reports. Of the 14 cases recently reported from USA, 1 (7%) died and 4 (29%) developed chronic kidney disease.

*S. pneumoniae* encodes many virulence factors, but only the secreted neuraminidase A (NanA) was reported to be attributed to HUS. Neuraminidase cleaves N-acetyl-neuraminic acid (sialic acid) residues on red blood cells (RBC), platelets and endothelial cells, and the results may lead to the exposure of the Thomsen-Friedenrich antigen (T antigen), and allow the circulating anti-T antigen antibodies to react with the exposed T antigen on cells. The role of neuraminidase(s) in pneumococcal diseases is illustrated based on the fact that pneumococci produce two or three distinct neuraminidases, which are NanA, NanB, and NanC. All three neuraminidases have typically signal peptides for secretion, wherein NanA, unlike NanB and NanC, contains a C-terminal cell surface anchorage domain. NanA and NanB expose host cell surface receptors for pneumococcal adherence by cleaving sialic acid from the glycans and mucin of cell surface, and thereby it promotes the pneumococcal colonization on the upper respiratory tract. In in vivo study, a NanA mutant was cleared from the nasopharynx, trachea, and lungs within 12 hours postinfection, while a NanB mutant persisted but did not increase in either the nasopharynx, trachea, or lungs. However, the role of NanC remains unknown.

The nonvaccine serotypes have been emerging after the use of vaccines. Moreover, nothing worse than the fact that nonvaccine strains usually displayed increase antimicrobial resistance and virulence. This is the reason why the issue of pneumococcal infection remains to be a global public health challenge. Thus, continued efforts to develop new diagnostic methods and to develop vaccines with expanded or universal coverage, such as a universal protein vaccine, are critically required for the better control of the pneumococcal infections.

SUMMARY OF THE INVENTION

Based on our finding that *S. pneumoniae* isolates causing HUS, were mostly found to produce all of the three neuraminidases, including NanA, NanB, and NanC, we designed three primer sets to detect and clone these pneumococcal neuraminidase genes in this invention. The three recombinant neuraminidases combined together serve as an ideal vaccine candidate because it presents the best protective efficacy against pneumococcal infection in mice, compared to the others. In one embodiment, the present invention provides a method of molecular detection of pneumococcal diseases by PCR in a *S. pneumoniae*-infected sample to amplify three neuraminidase genes based on the sequences of the three neuraminidase genes of *S. pneumoniae* strain CGSP14. In another embodiment, the present invention provides a method of generating immunization in humans and animals against *S. pneumoniae* infection using a composition comprising the three recombinant neuraminidases, including NanA, NanB, and NanC.

In still another embodiment, the present invention provides protection against *S. pneumoniae* infection using three pneumococcal neuraminidases as antigens in active immunization, and/or using anti-neuraminidase antibodies for passive immunization. In a further embodiment, the present invention provides a method of detecting inhibition of a neuraminidase activity by antibody or antiserum using flow cytometry. In still a further embodiment, the present invention is able to detect the presence of any of the three neuraminidases in the *S. pneumoniae*-infected samples using the anti-neuraminidase antibodies generated from neuraminidases-immunized humanized animals.

Figure 6A:
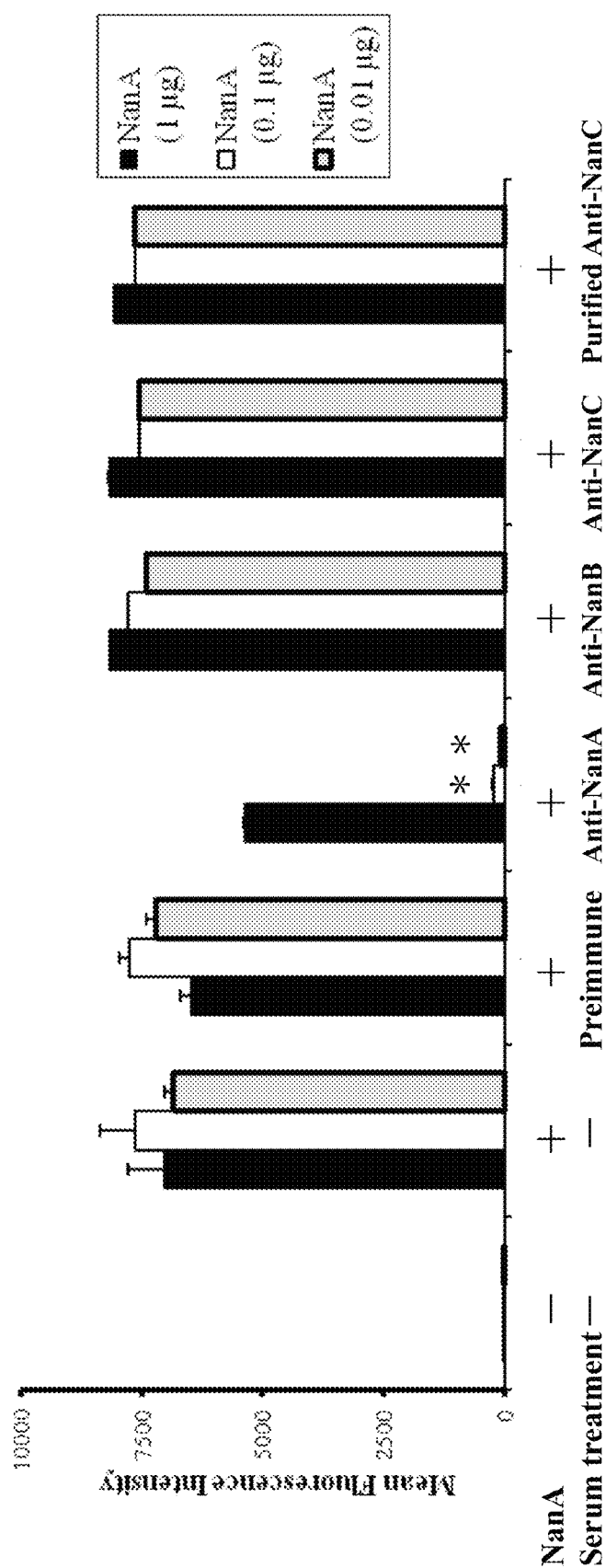
Figure 6B:
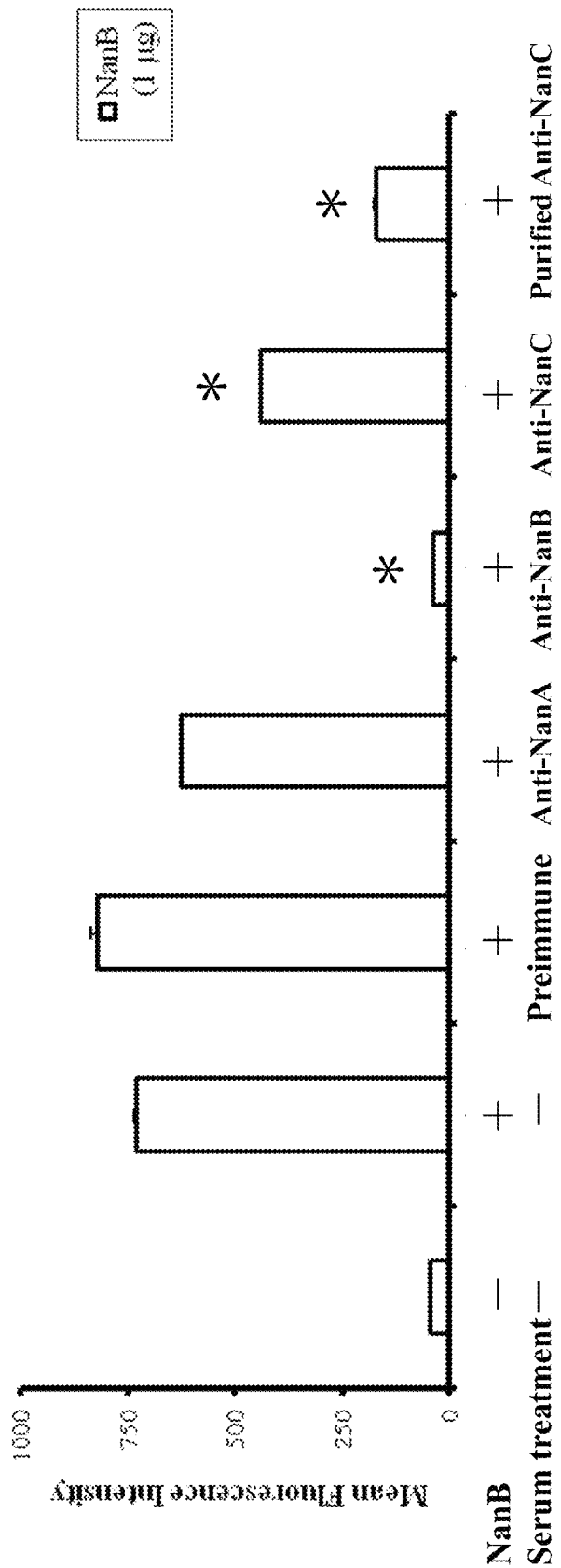
Figure 6C:
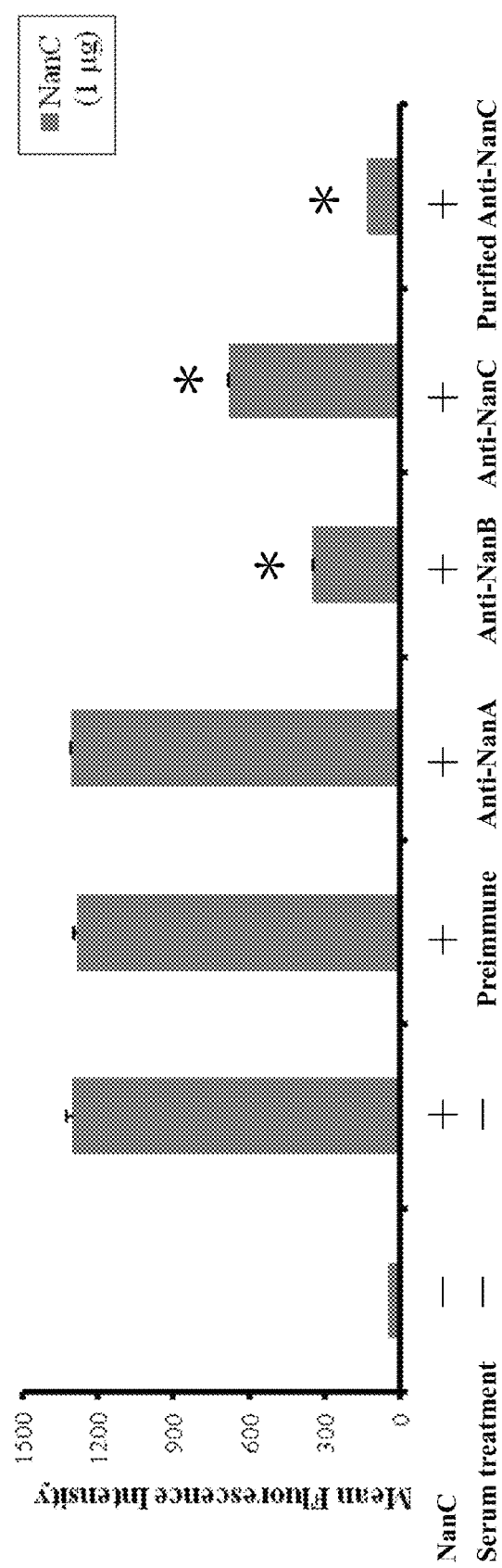

FIGS. 6A-6C: Inhibition of neuraminidase activity by the anti-serum raised from neuraminidase-immunized rabbit. Neuraminidase-mediated TA antigen exposure presented on RBC cells was quantified by flow cytometry analysis, where FITC-labeled PNA lactin was used for the recognition of TA antigen. Prior to the quantification of TA exposure, an individual neuraminidase (including NanA, NanB, and NanC) was individually added for the treatment with different anti-neuraminidase anti-sera (30 μg/mL), including purified anti-NanC antiserum. (Figure A) NanA added for the treatment of rabbit anti-neuraminidase anti-serum were 1 μg (black bars), 0.1 μg (white bars), and 0.01 μg (grey bars). (Figure B) NanB added for the treatment of rabbit anti-NanB anti-serum was 1 μg (white bars). (Figure C) NanC added for the treatment of rabbit anti-NanC anti-serum was 1 μg (grey bars). * indicates p<0.05, when compared to the controls (only neuraminidase addition without serum treatment; neuraminidase addition with pre-immune serum treatment).

Figure 7A:
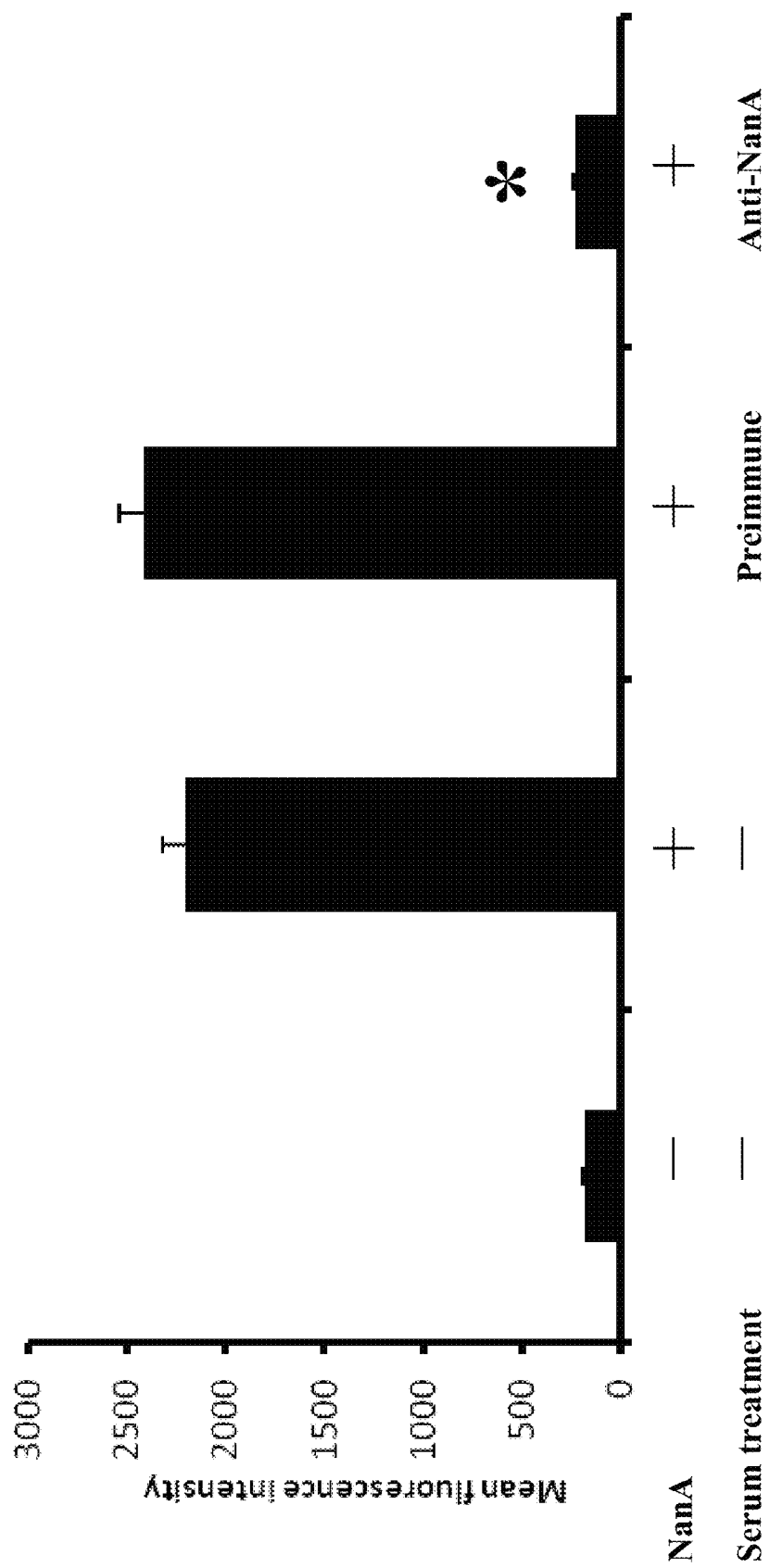
Figure 7B:
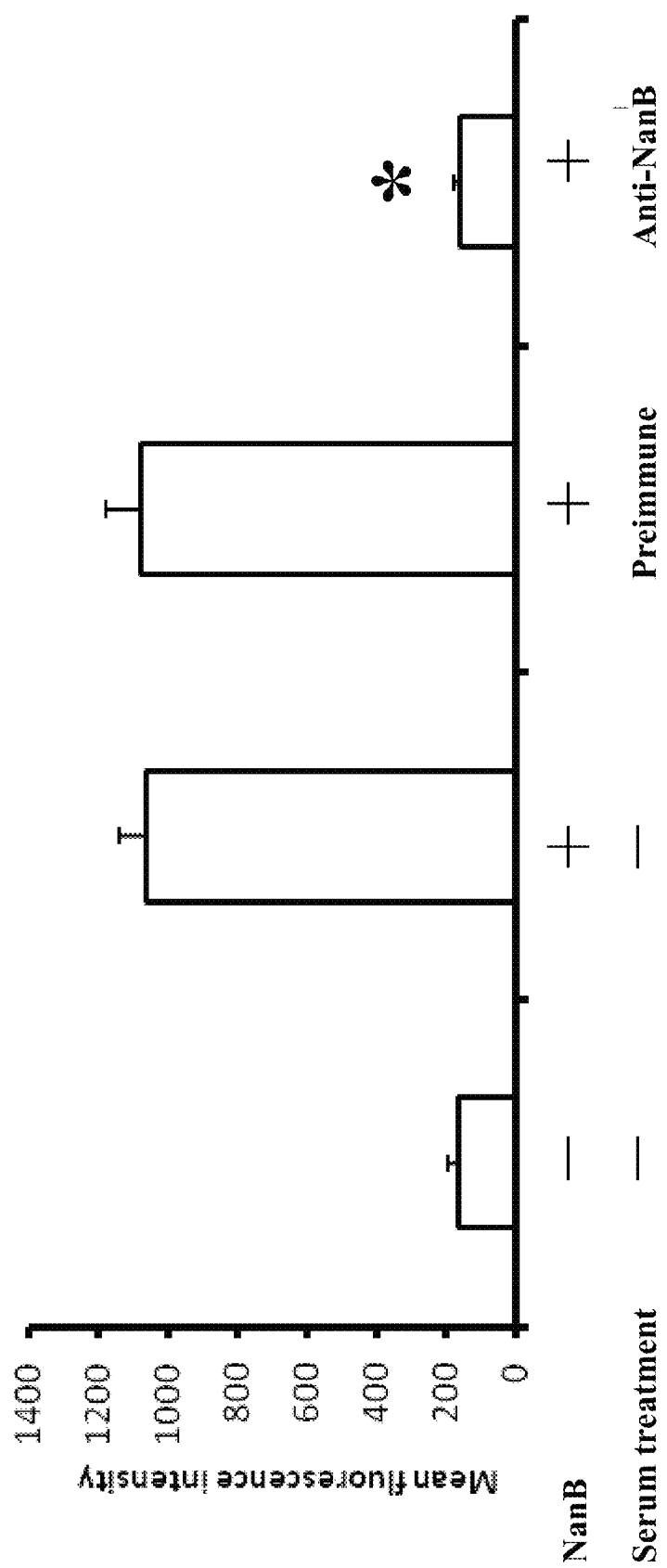
Figure 7C:
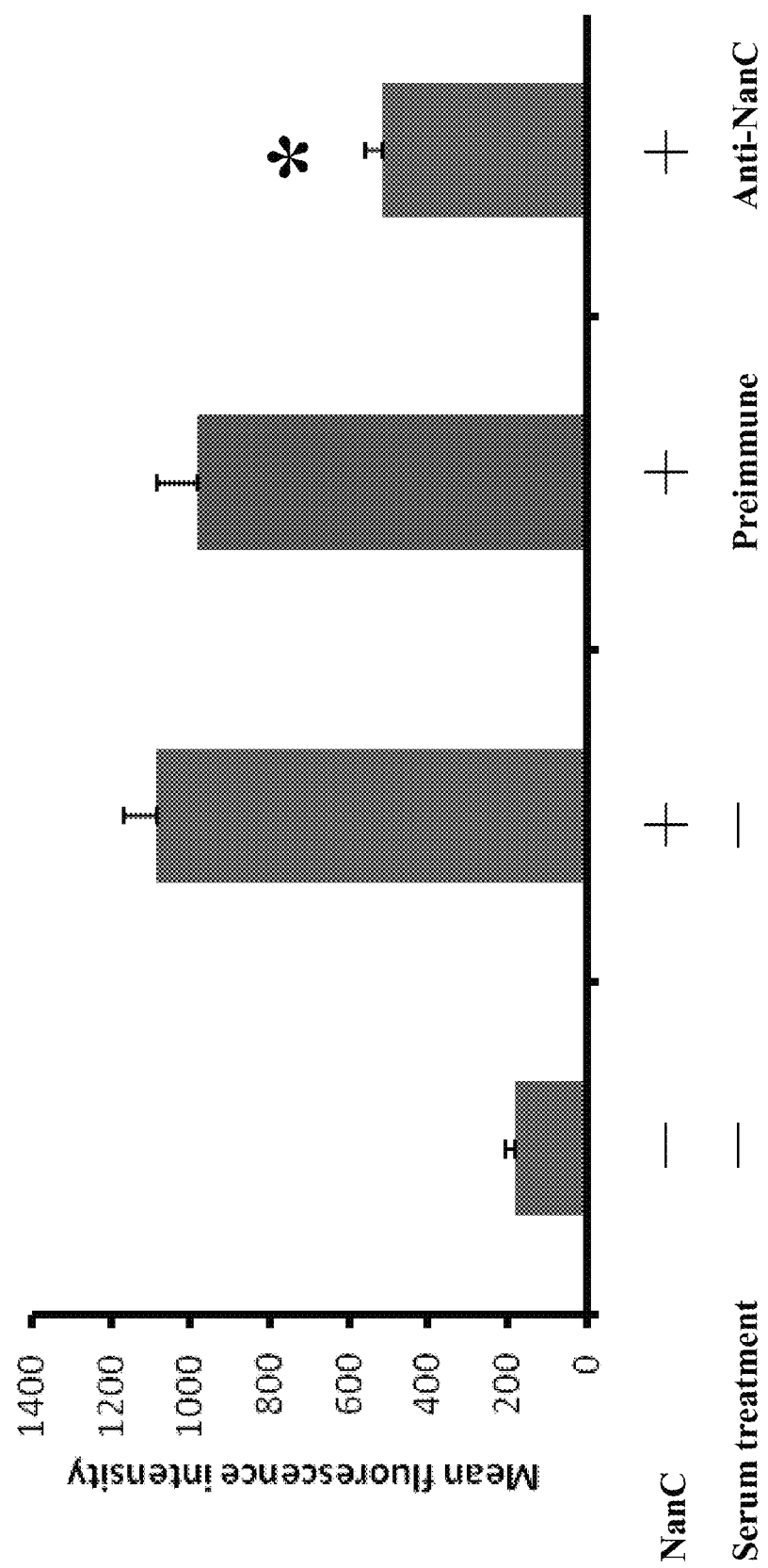

FIGS. 7A-7C: Inhibition of neuraminidase activity by the anti-serum raised from neuraminidase-immunized mouse. Neuraminidase-mediated TA antigen exposure presented on RBC cells was quantified by flow cytometry analysis, where FITC-labeled PNA lactin was used for the recognition of TA antigen. Prior to the quantification of TA exposure, an individual neuraminidase (including NanA, NanB, and NanC) was added for the treatment with specific anti-neuraminidase anti-sera (30 μg/mL). (Figure A) NanA added for the treatment of mouse anti-NanA anti-serum was 0.1 μg. (Figure B) NanB added for the treatment of mouse anti-NanB anti-serum was 1 μg. (Figure C) NanC used for the treatment of mouse anti-NanC anti-serum was 1 μg. * indicates p<0.05, when compared to the controls (only neuraminidase addition without serum treatment; neuraminidase addition with pre-immune serum treatment).

DETAILED DESCRIPTION OF THE INVENTION

The detailed description set forth below is intended as a description of the presently exemplary device provided in accordance with aspects of the present invention and is not intended to represent the only forms in which the present invention may be prepared or utilized. It is to be understood, rather, that the same or equivalent functions and components may be accomplished by different embodiments that are also intended to be encompassed within the spirit and scope of the invention.

Unless defined otherwise, all technical and scientific terms used herein have the same meaning as commonly understood to one of ordinary skill in the art to which this invention belongs. Although any methods, devices and materials similar or equivalent to those described can be used in the practice or testing of the invention, the exemplary methods, devices and materials are now described.

All publications mentioned are incorporated by reference for the purpose of describing and disclosing, for example, the designs and methodologies that are described in the publications which might be used in connection with the presently described invention. The publications listed or discussed above, below and throughout the text are provided solely for their disclosure prior to the filing date of the present application. Nothing herein is to be construed as an admission that the inventors are not entitled to antedate such disclosure by virtue of prior invention.

A. Detection of Neuraminidase Genes nanA, nanB and nanC of *S. pneumoniae*

NanA and NanB have been considered to be virulence factors of *S. pneumoniae*; however, NanC remains poorly understood. The nanC gene was found in the genome of a serotype 14 strain that was isolated from a child with HUS. In this invention, we confirmed that the *S. pneumoniae* neuraminidase genes nanC as well as nanA and nanB are important virulence factors. Three primer sets for polymerase chain reaction (PCR) are designed for the detection and cloning of the neuraminidase genes that are nanA (Seq. ID No. 1), nanB (Seq. ID No. 2), and nanC (Seq. ID No. 3), based on the genomic sequence of *S. pneumoniae* strain CGSP14 with NCBI accession number NC_010582. The detection comprises those pneumococcal isolates, especially for invasive pneumococcal diseases, including HUS.

Primer Design to Amplify nanA, nanB and nanC

Three primer sets used for PCR-amplification of nanA, nanB and nanC are designed with two purposes: one is provided for gene detection, and the other for gene cloning into an expression vector as described later.

1. For nanA amplification based on Seq. ID No. 1:

```
NanA-ATG-     5'-AGATCTGGGTACCATGTCTTATTTCAGAA ATCG
KpnI:

NanA-TAA-     5'-TGGTG CTCGA GTTGTTCTCTCTTTTTCCCT A
XhoI:
```

The expected size of amplicon is 2964 bp long.

2. For nanB amplification based on Seq. ID No. 2:

```
NanB-ATG-     5'-AGATCTGGGTACCATGAATA
KpnI:         AAAGAGGTCTTTA

NanB-TAA-     5'-TGGTG CTCGA GTTTTGTTAA ATCATTAATT
XhoI:         TC
```

The expected size of amplicon is 2115 bp long.

3. For nanC amplification based on Seq. ID No. 3:

```
NanC-ATG-     5'-AGATCTGGGTACCATGAAAAAAAAT
KpnI:         ATTAAACA

NanC-TAA-     5'-TGGTG CTCGA GATTCTTTTTCAGATCTTCA
XhoI:         A
```

The expected size of amplicon is 2244 bp long.

In these primer sets, the bold sequences based on the neuraminidase genes are designed for the cloning of full length of genes; the underlined sequences GGTACC and CTCGAG are the KpnI and XhoI recognition sites, respectively, which are built in for cloning into an expression vector; and the plain sequences are extra-sequences which are generated for efficient digests by KpnI and XhoI.

Detection of Neuraminidase Genes nanA, nanB and nanC in Pneumococcal Isolates

The clinical data related to *S. pneumoniae* infection from Chang Gung Memorial Hospital (CGMH), Taoyuan, Taiwan were compiled in the study of this invention. The invasive pneumococcal disease (IPD) cases are defined as the isolates of *S. pneumoniae* from normally sterile sites, such as blood, cerebrospinal fluid, or pleural fluid. Patients hospitalized with HUS, associated with an IPD between January 2006 and December 2009, were children less than 18 years old. HUS is defined according to the definition of Centers for Disease Control and Prevention (CDC, 1997). For HUS diagnosis, coagulation studies were examined, and the presence of normal fibrinogen was used to rule out disseminated intravascular coagulopathy. HUS patients enclosed were confirmed for Thomsen-Friedenrich antigen (TA) activation by the peanut (*Arachis hypogaea*) lectin agglutination method.

Figure 1:
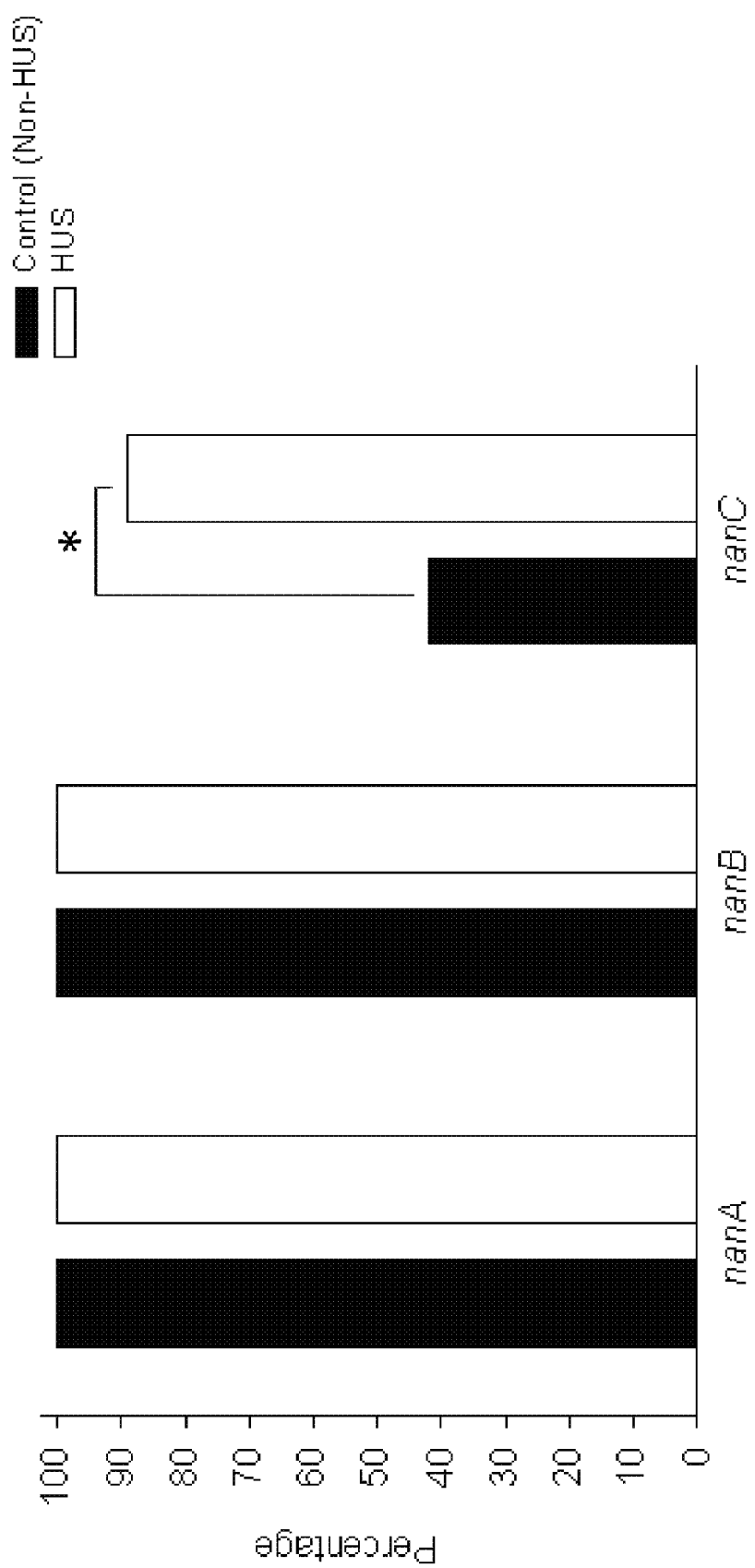
FIG. 1: Percentage of neuraminidase genes nanA, nanB and nanC among *Streptococcus pneumoniae* isolates derived from HUS patients and non-HUS controls (nanC 89% vs. 41% *p<0.005).

In our study, 18 *S. pneumoniae* isolates from patients with HUS and 54 from non-HUS patients were collected for detecting the neuraminidase genes by PCR using the primer sets designed as the above section. *S. pneumoniae* intrinsically carry nanA and nanB, as 100% of isolates from both groups have the two genes; however, relative to 16 (89%) of the HUS isolates that harbor nanC, only 22 (41%) isolates from the 54 controls carry the gene (P=0.002) (FIG. 1).

Among the total of 72 *S. pneumoniae* isolates examined in this invention, 72% (21/29) of the serotype 14 isolates contained nanC and 48% (14/29) of the patients infected by this serotype caused necrotizing pneumonia. Furthermore, 56% (5/9) of the serotype 3 isolates contained nanC and 44% (4/9) caused necrotizing pneumonia. Although 60% (6/10) of the serotype 6B and 71% (5/7) of the 23F also contained nanC, the two serotypes less commonly had necrotizing pneumonia and HUS. In contrast, 19F and its two allele MLST variant 19A seldom contained nanC (only 1 19F), but 38% (3/8) of the patients infected by 19A and 22% (2/9) by 19F had necrotizing pneumonia. The difference showed marginally significant (P=0.051) between HUS isolates and those specifically from necrotizing pneumonia patients.

Given the fact that almost all patients with HUS caused necrotizing pneumonia, the result suggests that NanC should be a virulence factor for necrotizing pneumonia as well as for HUS. We conclude that nanC gene is one of important microbe factors for necrotizing pneumonia and HUS caused by *S. pneumoniae* serotypes, not just by serotype 14 as mentioned previously.

B. Biofunctional Assays of Neuraminidase NanA, NanB and NanC of *S. pneumoniae* Strains CGSP14

In order to analyze the biofunction of neuraminidases in this invention, the recombinant NanA, NanB, and NanC of *S. pneumoniae* strains CGSP14 were cloned by using the primer sets as described in the previous section, and also characterized for their features. These biofunctional assays characterized include the exposure of the Thomsen-Friedenrich antigen (TA) and substrate specificity as the follows.

Cloning, Expression, and Purification of Recombinant NanA, NanB, and NanC

Figure 2:
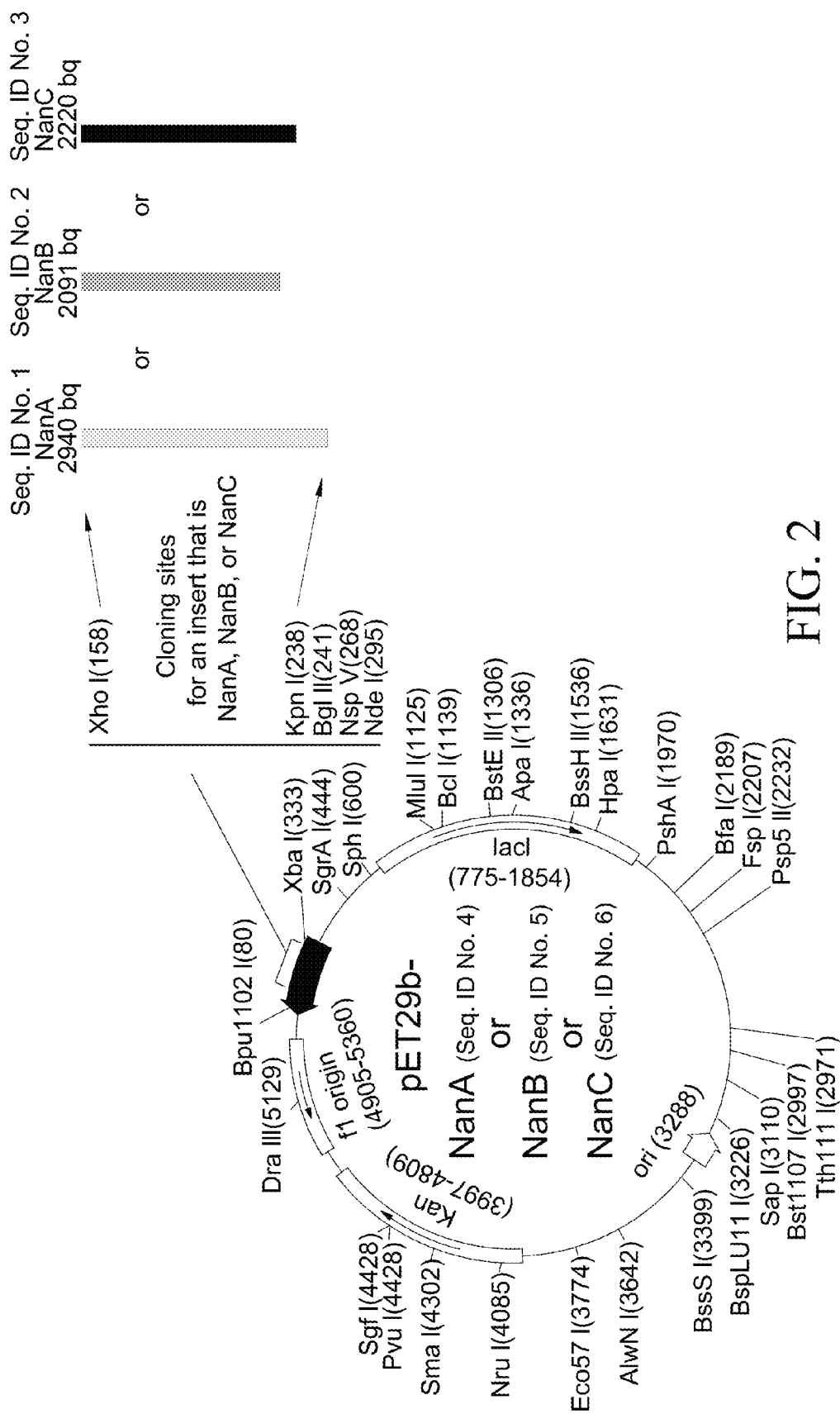
FIG. 2: Schematic diagram of the recombinant clones. Each PCR-amplified amplicon of neuraminidase genes (including nanA, nanB, and nanC), which sequences were based on the genomic sequence of *S. pneumoniae* strain CGSP14, was cloned into an expression vector pET29b through restriction enzyme digest by KpnI and XhoI. Seq. ID (from No. 1 to No. 6) indicates individual sequences among those genes and clones.

Referred to FIG. 2, genes nanA (Sequence ID No. 1), nanB (Seq. ID No. 2), and nanC (Seq. ID No. 3) based on the genomic sequence of *S. pneumoniae* strain CGSP14 with NCBI accession number NC_010582 were PCR-amplified and cloned into the expression vector pET29b (NOVAGEN, MERCK, Darmstadt, Germany) using KpnI and XhoI as cloning sites; the resulting clones are pET29b-NanA (Seq. ID No. 4), pET29b-NanB (Seq. ID No. 5), and pET29b-NanC (Seq. ID No. 6), respectively. The recombinant proteins, thus, can be inducibly over-expressed by the supplement of isopropyl β-D-1-thiogalactopyranoside (IPTG, 1 g/mL) in any Gram-negative bacteria, such as *Escherichia coli* BL21 (DE3). *E. coli* clones were cultured in Luria-Bertani (LB) broth at 37° C. for 4 hours with IPTG induction, where the original culture was 1/100 dilution with LB broth prior to IPTG induction. Because the recombinant NanA, NanB and NanC are histidine-tagged fusion proteins with the sizes of 100, 80, and 85 kDa, respectively, they may be easily purified according to the manufacturer's instructions for any kinds of $Ni^{2+}$ affinity chromatography, such as Nickel-Chelating Resin (Invitrogen, Carlsbad, Calif., USA).

TA Exposure Activities on Cells Used to Confirm the Features of Recombinant NanA, NanB and NanC Referred to FIGS. 3A-3D, the TA exposure activities of the recombinant neuraminidases were tested.

Lectins are usually used to recognize glycoconjugate residues (such as TA antigen) on cells. Fluorescein-labeled peanut agglutinin (PNA; Vector Laboratories, Inc., Burlingame, Calif. 94010, U.S.A.) is commonly used to detect TA on cells. Fluorescein-labeled *Sambucus Nigra* lectin (SNA; Vector Laboratories, Inc., Burlingame, Calif. 94010, U.S.A.) and biotinylated *Maackia Amurensis* lectin II (MAL II; Vector Laboratories, Inc., Burlingame, Calif. 94010, U.S.A.) are applied to recognize α2-6 and α2-3 sialyl linkages, respectively.

For the detection of the glycoconjugates on red blood cell (RBC), freshly collected blood samples from healthy volunteers were used to prepare the RBC fraction according to the method described in AABB Technical Manual, 14th Edition (http://freetechebooks.com/ebook-2011/aabb-technical-manual.html). RBC ($3\times10^7$ cells/mL), A549 (human epithelial lung cell line; ATCC® Number: CCL-185™) and HK-2 (human kidney 2 cell line; ATCC® Number: CRU-2190™) cells ($1\times10^6$ cells/mL) were cultured in Dulbecco's modified Eagle's medium (DMEM) plus Ham F12 medium, and treated with neuraminidase NanA, NanB or NanC (1 μg for RBC; 0.1 μg for A549 and HK-2). The mixture was incubated at 37° C. for 1-2 hours. For flow cytometric (FACScan, Becton Dickinson, USA) analysis, 10,000-20,000 cells were used, and cell labeling with each of lectins, including PNA, SNA and MAL II was done at 4° C. for one hour, rather than higher temperature (such as 37° C.) and longer time period (such as overnight) to cause cell agglutination, which would jam flow analysis. Biotinylated MAL II labeling can be observed by using fluorescein-conjugated streptavidin. Furthermore, to observe for cell agglutination by microscopy, 20 μl aliquots of lectin-labeled RBC were incubated at 37° C. for 30 minutes.

Figure 3A:
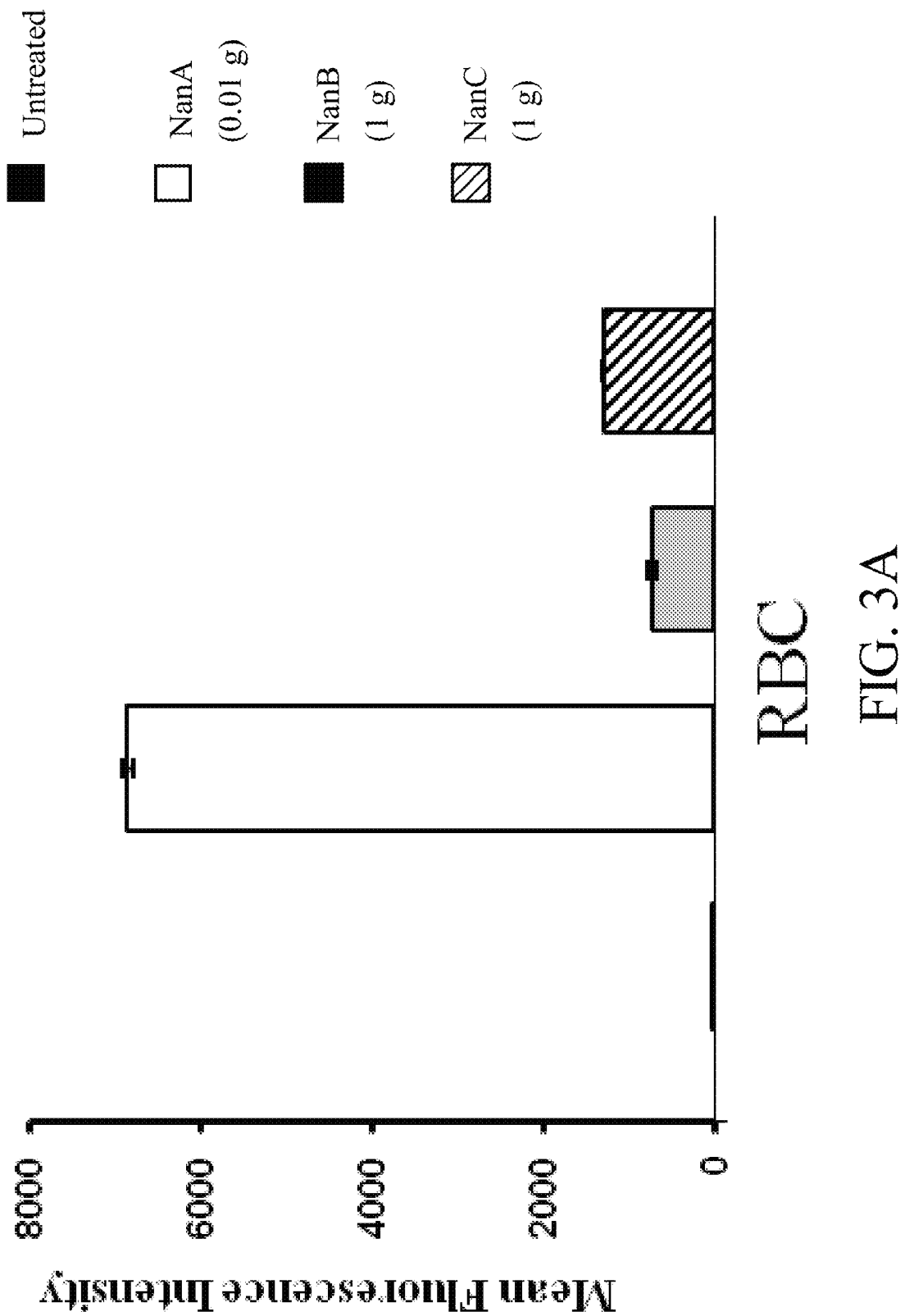
FIGS. 3A-3D: Thomsen-Friedenrich antigen (TA) exposure on cells. PNA lectin binding was used to detect the TA by flow cytometry. Numbers indicate fluorescence counts of samples, which are untreated cells (black), NanA-treated (white), NanB-treated (grey), and NanC-treated (hatched). NanA (0.01 Idg), NanB (1 μg) and NanC (1 μg) can expose TA on RBC (Figure A). NanA, NanB and NanC (all were 1 μg) can expose TA on A549 (Figure B) and HK-2 cells (Figure C). Twenty μL aliquots of PNA lectin labeled RBC used for flow cytometric analysis were incubated at 37° C. and observed under microscope to verify agglutination. Agglutination of RBC was observed when treated with NanA, NanB and NanC (0.1 μg) (Figure D).
Figure 3B:
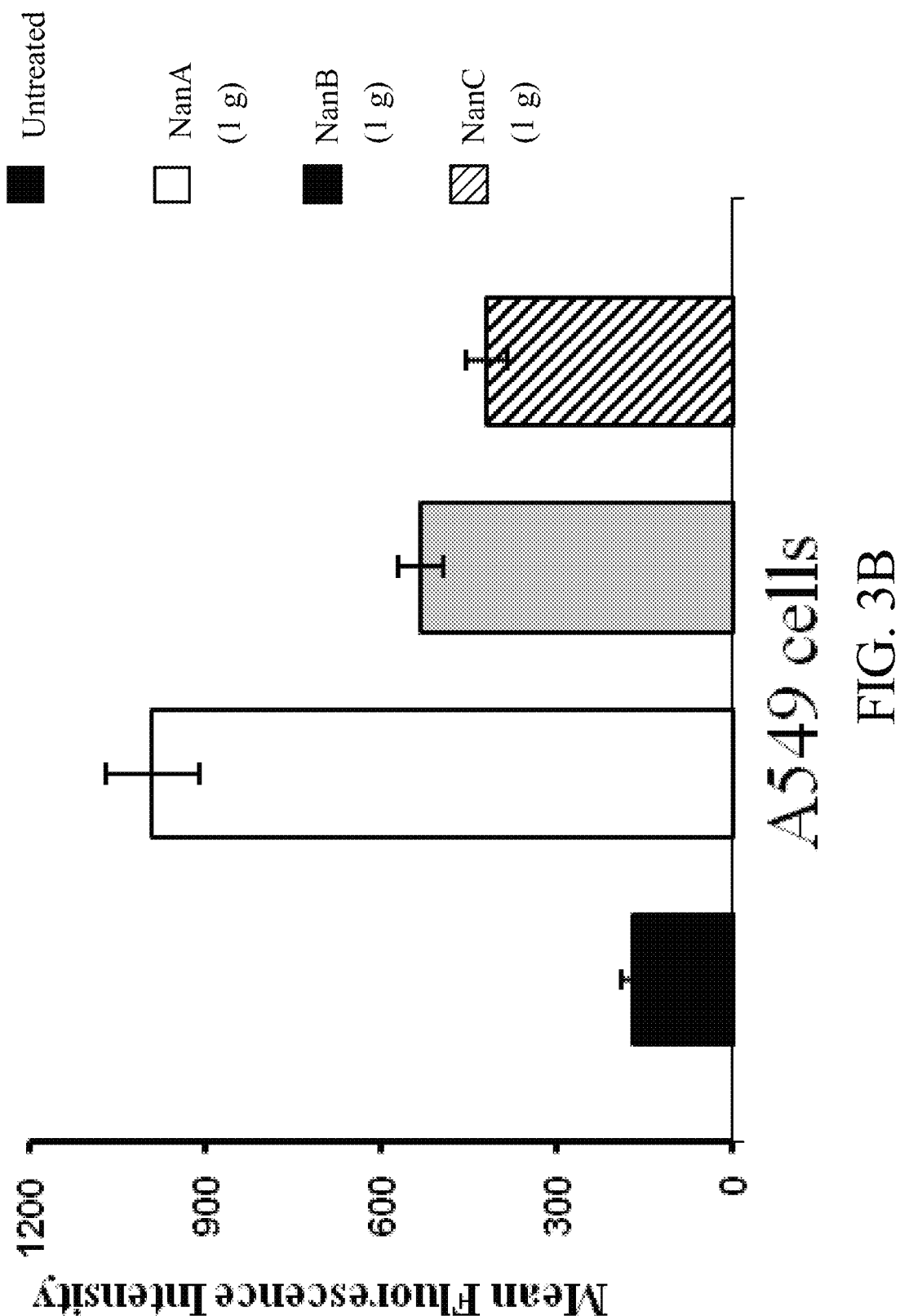
Figure 3C:
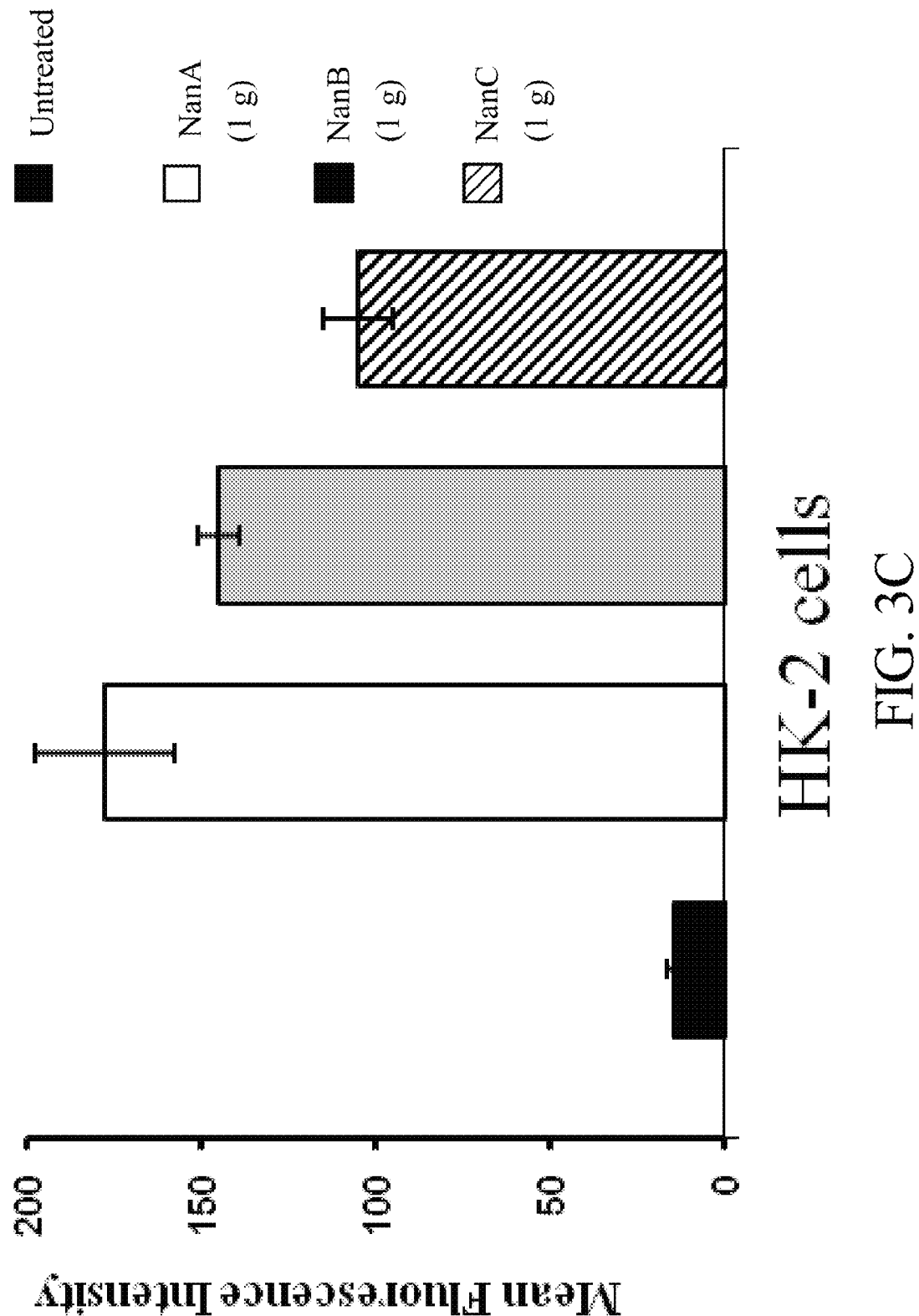
Figure 3D:
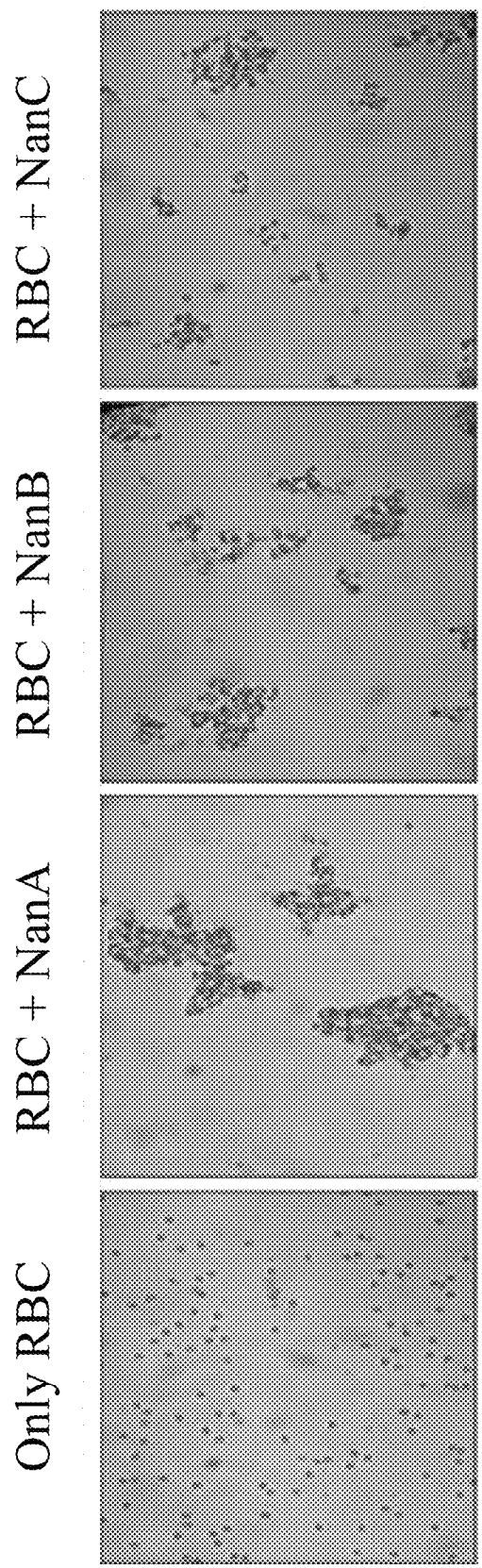

As shown in a previous report, TA exposure on RBC, platelets and glomeruli is mediated by the secreted NanA in pneumococcal infection. To proof whether NanC was also a potential virulence factor associated with HUS, the ability of NanC was analyzed to expose TA on cells. When RBC, A549 and HK-2 cells were treated with the recombinant NanB and NanC, TA exposure was detected (FIGS. 3A, 3B, and 3C). On RBC, the TA exposure activity of NanA had shown to reach a plateau when NanA used was more than 0.01 μg. Thus, 0.01-μg NanA was used to compare with 1-μg NanB and 1-μg NanC. The results showed that the activity of NanA was $9.4\times10^2$ and $5.3\times10^2$ times higher than those of NanB and NanC, respectively. When lectin-PNA was used to verify TA exposure on RBC, NanA-treated RBC showed larger aggregates under microscopic examination, compared to the treatments by NanB and NanC (FIG. 3D), whereas no agglutination was present with PNA in the case of untreated RBC. NanA activity shown on A549 cells was 2.2 and 3.3 times higher than NanB and NanC, respectively, while NanA activity on HK-2 cells was 1.5 times higher than both NanB and NanC.

C. Protection by Immunization Using Recombinant NanA, NanB, and NanC as Antigens In order to develop an ideal vaccine against pneumococcal infection, particularly to be a universal protein vaccine, we chose three pneumococcal neuraminidases as a vaccine material to immunize mice, while PPV23 vaccine was used as a positive control. Meanwhile, the neuraminidase-immunized antisera were also applied for the inhibition assay against the neuraminidase activity.

Vaccination Against *S. pneumoniae* in Mice

Figure 4:
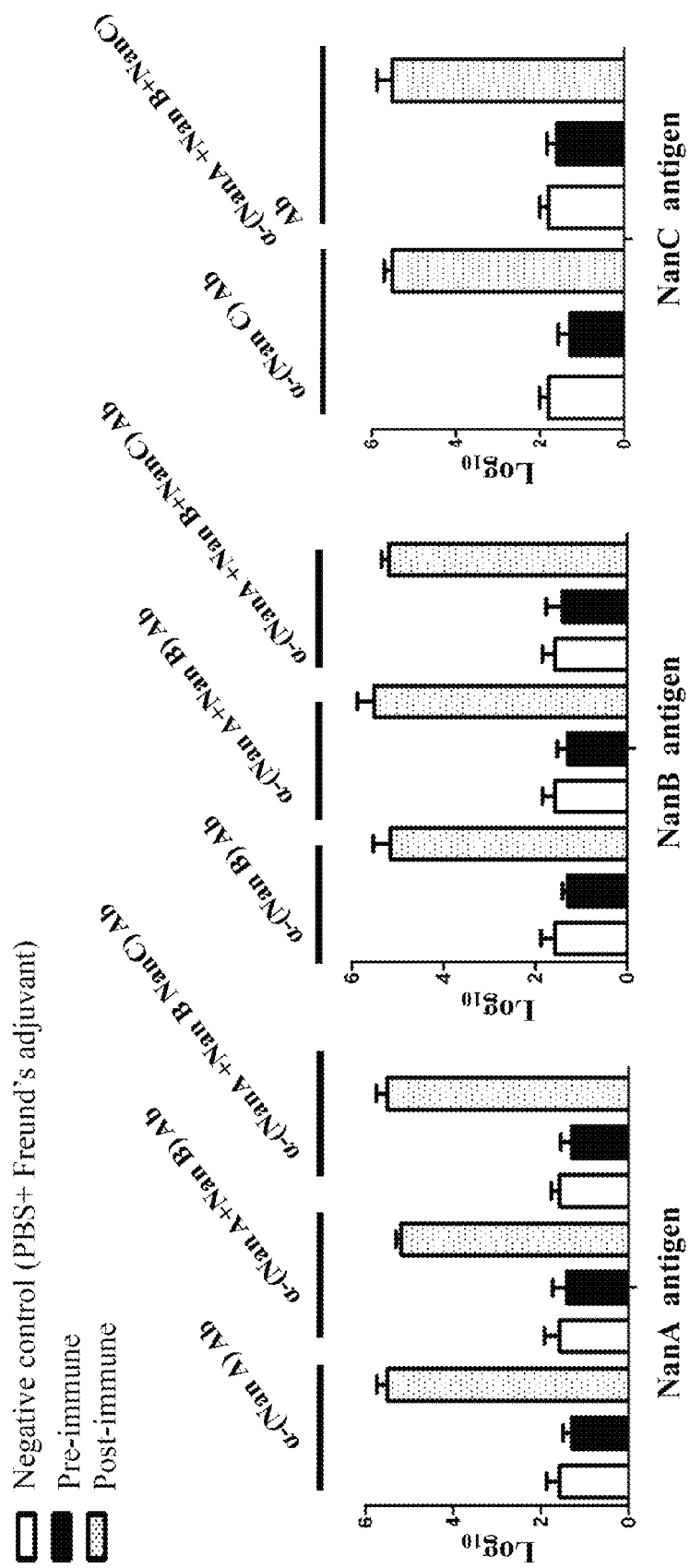
FIG. 4: Confirmation of mouse polyclonal antisera against neuraminidase(s) by enzyme-linked immunosorbent assay (ELISA). Mouse post-immune (grey box) antisera against neuraminidase(s) antigens from different combinations, including individual neuraminidase (NanA, NanB, or NanC), neuraminidase A+B (NanA+NanB), and neuraminidase A+B+C (NanA+NanB+NanC), were tested by ELISA, while the sera from pre-immune (black box) and negative control (only PBS plus Freund's adjuvant without antigen; white box) were also examined. The antigen-antibody interactions were quantified by using the peroxidase-conjugated goat anti-mouse IgG (Sigma) as a secondary antibody and tetramethylbenzidine/peroxide (R&D Systems, Minneapolis, Minn., USA) as a color-developing substrate under the analysis of ELISA reader with the maximum absorbance band at a wavelength of 405 nenometer (EMax, Molecular Devices, Sunnyvale, Calif. 94089 USA). The value was presented by the logarithm of the value on y-axis.
Figure 5:
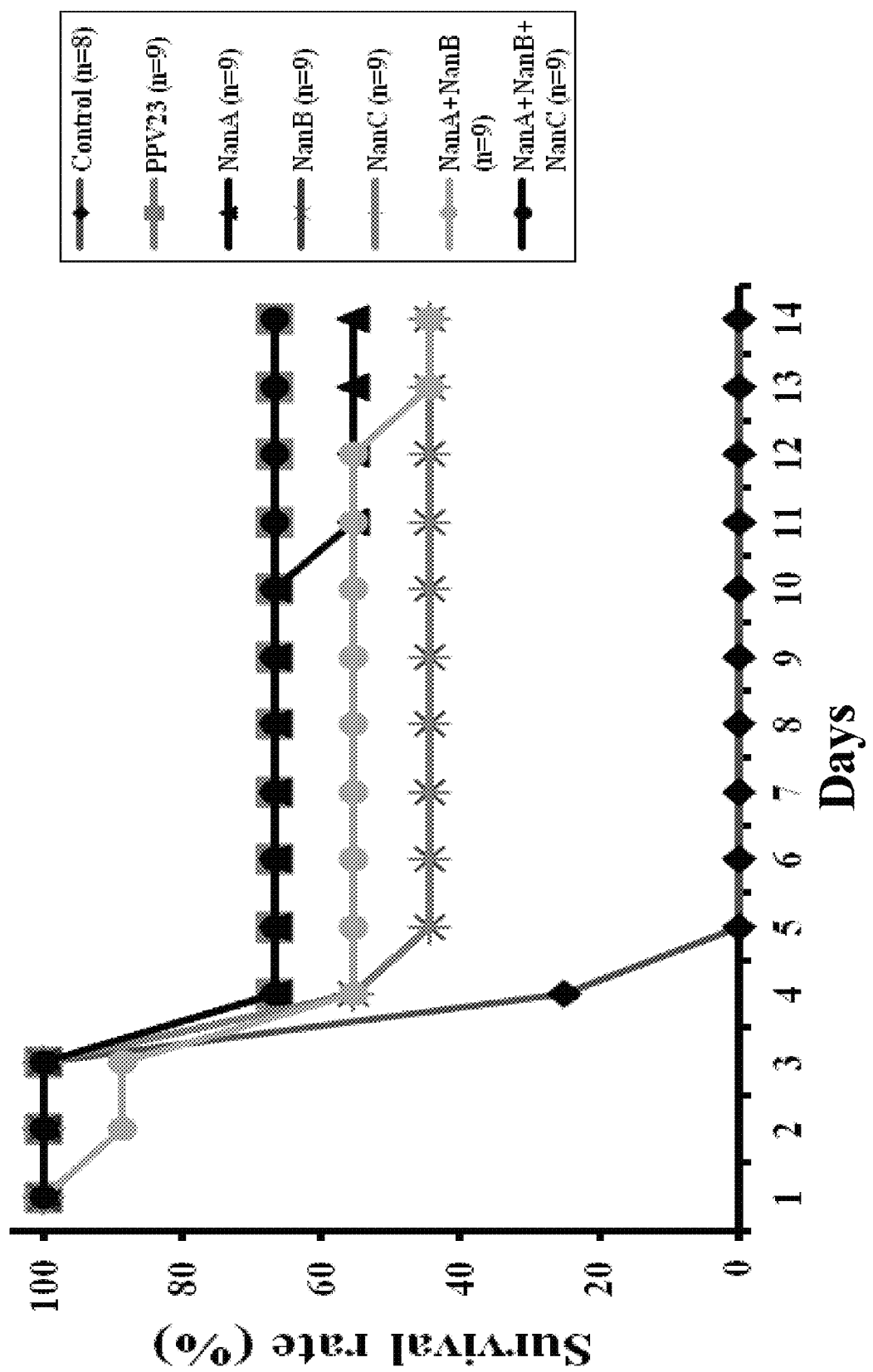
FIG. 5: Vaccination tests. The individual or combination of three neuraminidases, NanA, NanB and NanC with 10 μg of each enzyme, were applied as antigens to immunize mouse (SALE/C, one month old) four times at 2-week interval, while PPV23 vaccine and a negative control (PBS+Freund's adjuvant) were taken for comparison. Thereafter, *S. pneumoniae* serotype 3 (3×10³ cfu) was used to challenge those neuraminidase-immunized mice. Freund's complete adjuvant for the first time immunization and Freund's incomplete adjuvant for the last three immunizations were used with the ratio of 1:1 to the antigen(s). Mice survival rate (%) was determined during 14 days feeding after four times neuraminidase immunization and a subsequent *S. pneumoniae* challenge. N is the number of mice for test.

Referred to FIGS. 4 and 5, the recombinant NanA, NanB and NanC were used as the antigens to protect the mice against *S. pneumoniae* in mice in this invention. For comparison of vaccination, the individual or combination of neuraminidases NanA, NanB and NanC (10 μg/each enzyme) were applied to immune mice (BALB/C, one month old) four times at 2-week interval prior to *S. pneumoniae* ($3 \times 10^3$ cfu) challenge, while 23-valent Pneumovax® (Merck Sharp & Dohme Corp., N.J. 08889, USA) polysaccharide vaccine (PPV23) and only phosphate buffered saline (PBS) were used as positive and negative controls, respectively. Freund's complete adjuvant for first time immunization and Freund's incomplete adjuvant for the last three immunizations were used with the ratio of 1:1 to the antigen(s).

To confirm the efficacy of mouse polyclonal anti-neuraminidase(s) antisera which were immunized by neuraminidase(s), we performed enzyme-linked immunosorbent assay (ELISA) which is based on the antigen-antibody sandwich principle. For ELISA test, the neuraminidase was first coated on an ELISA plate (Corning Incorporated, Corning, N.Y., USA). The anti-neuraminidase antiserum raised from mouse was then added to test how much antiserum was able to specifically bind on ELISA plate, and the antigen-antibody interaction was quantified by goat HRP-conjugated antimouse immunoglobulin G (IgG) as a secondary antibody (Millipore, Billerica, Mass. 01821, USA) and TMB/peroxide (R&D Systems, Minneapolis, Minn., USA) as a color-developing substrate. The post-immune antisera against neuraminidase(s) from different groups of combinations were tested, while the control sera from the pre-immune and the negative control with only PBS plus Freund's complete/incomplete adjuvants were also examined (FIG. 4). The value of antigen-antibody interaction was measured and presented logarithmically, as shown in FIG. 4. The results showed that each value of neuraminidase-immunized antisera, compared to the control sera, was 3-4 logarithm folds increase, revealing that each of three neuraminidases is an ideal antigen for immunization (FIG. 4).

For development of mouse vaccine against *S. pneumoniae*, the individual or combination of three neuraminidases, NanA, NanB and NanC with 10 μg of each enzyme, were applied to immunize nine mice (BALE/C, one month old) four times at 2-week interval, while PPV23 vaccine and a negative control (PBS+Freund's adjuvant) were taken for comparison. Thereafter, *S. pneumoniae* serotype 3 ($3 \times 10^3$ cfu) was used to challenge those immunized mice (FIG. 5). Freund's complete adjuvant for the first time immunization and Freund's incomplete adjuvant for the last three immunizations were used to mix with the antigen(s) with the ratio of 1:1. Mouse survival rate (%) was determined during 14 days of feeding after four times neuraminidase immunization and a following challenge using *S. pneumoniae* serotype 3. As shown in FIG. 5, vaccination tests showed that the group with the combination of three neuraminidases (NanA+NanB+NanC) presented the same 67% survival rate as that using the PPV23 vaccine, which value was the highest when compared to the other groups with one or two of three neuraminidases. In this invention, the combination containing three neuraminidases (NanA, NanB, and NanC) together was evaluated to be the best vaccine candidate for vaccination against *S. pneumoniae* infection in mice, and it also would be an appropriate candidate as a kind of universal protein vaccine.

Inhibition of Neuraminidase Activity by Antibodies or Immunized Antisera

As referred to FIGS. 6A to 7C, the inhibition assay was taken to test how efficient the neuraminidase activity can be inhibited by neuraminidase-specific antisera. The antisera against individual neuraminidase (NanA, NanB or NanC) were raised from rabbits, and then tested for their inhibitory effect on the activities of neuraminidases. NanC antiserum was purified by Protein A Sepharose beads (GE Healthcare) to increase its inhibition efficiency. Different amounts of neuraminidases in 10-μL PBS were pre-incubated with 10-μL immunized serum for 5 minutes. The antiserum-treated neuraminidase was mixed with RBC cells ($4 \times 10^6$ cells/mL) for 2 hours of incubation at 4° C. Inhibition of neuraminidases (NanA, NanB, and NanC) activity by rabbit antisera was quantified by TA exposure on RBCs using flow cytometry, wherein the detection of TA exposure on RBC cells using FITC-labeled PNA lectin was described in previous section. If neuraminidase is neutralized by a specific anti-neuraminidase serum, the exposure of TA antigen on RBC cells, and the value of fluorescence intensity will be reduced.

As shown on y-axis of FIGS. 6A-6C, the activities of NanB and NanC for TA antigen exposure were naturally weaker than that of NanA. NanA activity was completely inhibited by 30 μg anti-NanA antiserum when both 0.1-μg and 0.01-μg NanA were used, while only 20% activity was inhibited when 1-μg NanA was used (FIG. 6A). The 1 μg NanB activity was completely inhibited by 30 μg anti-NanB antiserum. However, only 40% NanC activity was inhibited by 30 μg anti-NanC antiserum, but 90% NanC activity was inhibited by 30 μg purified anti-NanC antiserum (FIG. 6C).

For cross-reactivity, antineuraminidase (including NanA, NanB and NanC) antisera were tested. Anti-NanA antiserum did not show inhibitory effect on the activity of NanB and NanC and vice versa. However, anti-NanB antiserum could inhibit NanC activity by 74%. Non-purified and purified anti-NanC antisera inhibited NanB activity by 40% and 76%, respectively.

The antisera from rabbit used to inhibit 50% neuraminidase activity were also assessed by titration test (data not shown). The dilution of anti-NanA antiserum for 50% NanA inhibition was 1, 8, and 32 for 1 μg, 0.1 μg and 0.01 μg, respectively. 50% NanB (1 μg) activity with anti-NanB antiserum was inhibited by 16 folds of dilution. The dilutions of non-purified and purified anti-NanC antisera to inhibit 50% NanC (1 μg) activity were 1 and 8, respectively.

Similar to the rabbit antineuraminidase antisera, the antineuraminidase antisera raised from mouse were also shown to specifically inhibit neuraminidase activities, as shown in FIGS. 7A-7C. The 30 μg mouse Anti-NanA and anti-NanB antisera enable to completely inhibit the activities of 0.1-μg NanA and 1 μg NanB, respectively. However, anti-NanC antiserum (30-μg) was only able to neutralize 50% NanC (1-μg) activity.

Taken together, the results indicated that each of anti-neuraminidase antisera raised from both rabbit and mice enables to specifically inhibit or neutralize its corresponding neuraminidase activity; however, only anti-NanB and anti-NanC antisera have cross-protection abilities against each other. Although the inhibition of the anti-NanC antiserum was not as efficient as those anti-NanA and anti-NanB antisera, the combination of NanC with NanA and NanB is the best candidate as a vaccine.

Having described the invention by the description and illustrations above, it should be understood that these are exemplary of the invention and are not to be considered as limiting. Accordingly, the invention is not to be considered as limited by the foregoing description, but includes any equivalents.

The invention claimed is:

1. A method for detecting the presence of any of the three neuraminidases thereof in the *Streptococcus pneumoniae*-infected samples using anti-neuraminidase antibodies, comprises steps of:
   using antibodies against neuraminidases NanA, NanB, and NanC, wherein said antibodies are prepared from the crude antisera and/or purified antibodies;
   detecting the presence of *Streptococcus pneumoniae* strains in *Streptococcus pneumoniae*-infected samples, wherein the technique used in detecting the presence of *Streptococcus pneumoniae* strains comprises enzyme linked immunosorbent assay (ELISA).

2. The method for detecting the presence of any of the three neuraminidase genes thereof in the *S. pneumoniae*-infected samples of claim 1, further comprises steps of amplifying pneumococcal HUS-associated genes in *S. pneumoniae*-infected samples by PCR and detecting said pneumococcal HUS-associated genes including nanA, nanB, and nanC.

* * * * *